(12) United States Patent  
Titus

(10) Patent No.: US 8,905,921 B2
(45) Date of Patent: Dec. 9, 2014

(54) OPTICAL COUPLER FOR AN ENDOSCOPE

(75) Inventor: James Sidney Titus, Sharon, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/398,277

(22) Filed: Feb. 16, 2012

(65) Prior Publication Data

US 2012/0209074 A1  Aug. 16, 2012

Related U.S. Application Data

(60) Provisional application No. 61/443,546, filed on Feb. 16, 2011.

(51) Int. Cl.
*A61B 1/06* (2006.01)
*A61B 1/00* (2006.01)
*A61B 1/04* (2006.01)

(52) U.S. Cl.
CPC ......... *A61B 1/00096* (2013.01); *A61B 1/00137* (2013.01); *A61B 1/00101* (2013.01)
USPC ............................. 600/175; 600/127; 600/129

(58) Field of Classification Search
CPC .................................................. A61B 1/00101
USPC .......... 600/127, 129, 175, 121–125, 172, 176
See application file for complete search history.

(56) References Cited

U.S. PATENT DOCUMENTS

| | | |
|---|---|---|
| 3,774,614 A | 11/1973 | Cook |
| 4,090,501 A | 5/1978 | Chaitin |
| 4,201,199 A | 5/1980 | Smith |
| 4,340,811 A | 7/1982 | Yamashita et al. |
| 4,681,093 A | 7/1987 | Ono et al. |
| 4,696,544 A * | 9/1987 | Costella ........................ 385/118 |
| 4,779,611 A | 10/1988 | Grooters et al. |
| 4,805,598 A | 2/1989 | Ueda |
| 4,878,725 A | 11/1989 | Hessel et al. |
| 4,881,810 A | 11/1989 | Hasegawa |
| 4,967,732 A * | 11/1990 | Inoue ............................. 600/139 |
| 5,050,585 A * | 9/1991 | Takahashi ..................... 600/123 |
| 5,237,984 A * | 8/1993 | Williams et al. .............. 600/124 |

(Continued)

OTHER PUBLICATIONS

Vinyl Sustainability Forum 2014, Title: Benefits of PVC, Date retrieved: Mar. 7, 2014 from wesite: http://www.pvc.org/en/p/benefits-of-pvc, pp. 1-4.*

(Continued)

*Primary Examiner* — Alireza Nia
(74) *Attorney, Agent, or Firm* — Quarles & Brady, LLP

(57) ABSTRACT

An optical coupler is disclosed with an attachment section for mounting at a distal end of an optical imaging device for visualizing a surface area covered with an opaque fluid and/or particulate matter. The coupler includes a visualization section at one end of the coupler that includes a proximal surface for engaging the distal end of the optical imaging device, an attachment section connected to and extending away from the visualization section, an outer surface spaced apart from the proximal surface, and may include a hollow instrument channel extending from the proximal surface toward the outer surface. This surface extends continuously from a first outer side boundary across to a second opposite outer side boundary of the visualization section. The visualization section can be formed from an elastic material capable of transmitting an optical image of the surface area. In one form, the material is a silicone gel or elastomer.

36 Claims, 20 Drawing Sheets

(56) References Cited

U.S. PATENT DOCUMENTS

| | | | |
|---|---|---|---|
| 5,329,935 A | 7/1994 | Takahashi | |
| 5,337,734 A | 8/1994 | Saab | |
| 5,342,388 A | 8/1994 | Toller | |
| 5,413,052 A | 5/1995 | Breezer et al. | |
| 5,443,781 A | 8/1995 | Saab | |
| 5,448,990 A | 9/1995 | De Faria-Correa | |
| 5,536,236 A | 7/1996 | Yabe et al. | |
| 5,555,129 A * | 9/1996 | Konno et al. | 359/569 |
| 5,575,291 A | 11/1996 | Hayakawa et al. | |
| 5,632,717 A * | 5/1997 | Yoon | 600/106 |
| 5,674,181 A | 10/1997 | Iida | |
| 5,725,474 A | 3/1998 | Yasui et al. | |
| 5,725,475 A | 3/1998 | Yasui et al. | |
| 5,738,629 A | 4/1998 | Moll et al. | |
| 5,743,851 A | 4/1998 | Moll et al. | |
| 5,771,327 A | 6/1998 | Bar-Or et al. | |
| 5,788,628 A | 8/1998 | Matsuno et al. | |
| 5,808,813 A | 9/1998 | Lucey et al. | |
| 5,840,014 A | 11/1998 | Miyano et al. | |
| 5,860,913 A | 1/1999 | Yamaya et al. | |
| 5,897,487 A | 4/1999 | Ouchi | |
| 6,059,719 A | 5/2000 | Yamamoto et al. | |
| 6,217,509 B1 | 4/2001 | Foley et al. | |
| 6,277,065 B1 | 8/2001 | Donofrio | |
| 6,306,081 B1 | 10/2001 | Ishikawa et al. | |
| 6,673,091 B1 | 1/2004 | Shaffer et al. | |
| 6,699,180 B2 | 3/2004 | Kobayashi | |
| 6,712,524 B2 | 3/2004 | Beatty et al. | |
| 6,723,350 B2 | 4/2004 | Burrell et al. | |
| 6,733,440 B2 | 5/2004 | Ailinger et al. | |
| 6,770,069 B1 | 8/2004 | Hobart et al. | |
| 6,855,108 B2 | 2/2005 | Ishibiki et al. | |
| 6,866,627 B2 | 3/2005 | Nozue | |
| 6,934,093 B2 | 8/2005 | Kislev et al. | |
| 7,033,317 B2 | 4/2006 | Pruitt | |
| 7,087,012 B2 | 8/2006 | Ishibiki | |
| 7,112,195 B2 | 9/2006 | Boll et al. | |
| 7,238,153 B2 | 7/2007 | Moriyama | |
| 7,245,813 B2 | 7/2007 | Brown et al. | |
| 7,537,561 B2 | 5/2009 | Yamaya et al. | |
| 7,553,278 B2 | 6/2009 | Kucklick | |
| 7,554,743 B2 | 6/2009 | Jiang et al. | |
| 7,621,868 B2 * | 11/2009 | Breidenthal et al. | 600/166 |
| 2002/0035311 A1 | 3/2002 | Ouchi | |
| 2004/0157073 A1 | 8/2004 | Burrell et al. | |
| 2004/0249246 A1 | 12/2004 | Campos | |
| 2004/0263613 A1 * | 12/2004 | Morita | 348/51 |
| 2004/0267092 A1 | 12/2004 | Ishibiki | |
| 2006/0084839 A1 | 4/2006 | Mourlas et al. | |
| 2006/0173241 A1 | 8/2006 | Ouchi et al. | |
| 2006/0200176 A1 * | 9/2006 | Matsuno et al. | 606/140 |
| 2006/0229662 A1 | 10/2006 | Finkielsztein et al. | |
| 2006/0270900 A1 | 11/2006 | Chin et al. | |
| 2007/0038043 A1 | 2/2007 | Gelikonov et al. | |
| 2007/0066870 A1 | 3/2007 | Ohashi et al. | |
| 2007/0293888 A1 | 12/2007 | Harren et al. | |
| 2008/0139885 A1 | 6/2008 | Knapp | |
| 2008/0262295 A1 | 10/2008 | Kendale et al. | |
| 2008/0306335 A1 | 12/2008 | Lau et al. | |
| 2009/0048486 A1 * | 2/2009 | Surti | 600/127 |
| 2009/0098409 A1 | 4/2009 | Yamada et al. | |
| 2009/0156898 A1 | 6/2009 | Ichimura | |
| 2009/0315989 A1 | 12/2009 | Adelson | |
| 2009/0326328 A1 | 12/2009 | Kucklick | |
| 2010/0026940 A1 * | 2/2010 | Takegami et al. | 349/102 |
| 2010/0121442 A1 | 5/2010 | Shea et al. | |
| 2010/0286475 A1 | 11/2010 | Robertson | |
| 2012/0232342 A1 * | 9/2012 | Reydel | 600/104 |

OTHER PUBLICATIONS

International Search Report and Written Opinion for PCT/US2012/025404, dated Sep. 21, 2012.

Kopp, et al., Chapter 9, Optical Principles of the Endoscope, Hysteroscopy: Visual Perspectives of Uterine Anatomy, Physiology & Pathology, 3rd Edition, Lippincott Williams & Wilkins, 2007, 19 pages.

Paxton, et al., An Experimental Investigation on the Development of Hydrogels for Optical Applications, Polymer Testing, 2003, 22(4):371-374, English Abstract.

Smeds, et al., Photocrosslinkable Polysaccharides for in situ Hydrogel Formation, Journal of Biomedical Materials Research, 2001, 54:115-121.

Uw Eye Research Institute, Newsletter, Point of View, Summer 2009, http://vision.wisc.edu/news_sum09.html, Printed Feb. 5, 2010.

Depth of Field, OPMI Application Tip #2, Informed for Medical Professionals in Neuro, ENT and Spine, 2nd Issue, Oct. 2006, Published by Carl Zeiss Surgical GmbH, Germany.

Zeng, et al., An Endoscope Utilizing Tunable-Focus Microlenses Actuated through Infrared Light, Solid-State Sensors, Actuators and Microsystems Conference, 2009, Transducers 2009, International, Issue 21-25, pp. 1214-1217, Abstract Only.

Zeng, et al., Tunable Liquid Microlens Actuated by Infrared Light-Responsive Hydrogel, Applied Physics Letters, 2008, 93:151101-1-151101-3.

Oil Immersion, From Wikipedia, http://en.wikipedia.org/wiki/Oil_immerson, Printed Sep. 7, 2010.

The Basics of Silicon Chemistry, Basic Silicon Production and Siloxane Polymerization, http://www.dowcorning.com/content/sitech/sitechbasics/siloxane_polymerization.asp, Copyright 2000-2010 Dow Corning Corporation.

Maquet Training Manual, Vasoview 6 Endoscopic Vessel Harvesting System, Cardiovascular, Copyright Maquet Cardiovascular LLC, Oct. 2008.

SmartGel Nye Nyogel OCK-451LPH Product Data Sheet, Nye Optical Products.

Optical Gels for Fiber-Optic Connectors and Splices—A Tutorial, Nye Optical Products, 6 pages.

Olympus Disposal Distal Attachment Product Data Sheet.

Olympus Technologies Evis Exera II, Learn About Wide—Angle, http://www.olympusamerica.com/msg_section/msg_endoscopy_technology.asp, Copyright 2010 Olympus America Inc.

Olympus Technologies Evis Exera II, Learn About Close Focus, http://www.olympusamerica.com/msg_section/msg_endoscopy_technology.asp, Copyright 2010 Olympus America Inc.

Olympus Colonoscopes Outpatient Doctor Surgery Center, http://outpatientsurgicare.com/index.PHP?Facilities:Technologies:Olympus_Colonoscopes&print, Printed Oct. 26, 2010.

Olympus Evis Exera Colonovideoscope/Sigmoidovideoscope, Olympus CF Type Q160L/I/S, Today's Most Versatile Choice for Colonoscopy, Product Data Sheet.

Olympus NA-11J-KB Product Data Sheet.

Sigma-Aldrich Poly(2-hydroxyethyl methacrylate) Product Data Sheet, http://www.sigmaaldrich.com/catalog/Product Detail, Copyright 2010 Sigma-Aldrich Co.

Sigma-Aldrich Poly(ethylene glycol) Product Data Sheet, http://www.sigmaaldrich.com/catalog/Product Detail, Copyright 2010 Sigma-Aldrich Co.

Sigma-Aldrich Poly(vinyl alcohol) Product Data Sheet, http://www.sigmaaldrich.com/catalog/Product Detail, Copyright 2010 Sigma-Aldrich Co.

Sigma-Aldrich Methacrylic acid Product Data Sheet, http://www.sigmaaldrich.com/catalog/Product Detail, Printed Sep. 3, 2010.

Cargille Laboratories, Inc. Material Safety Data Sheet—Cargille Optical Gel Code 0607, Jun. 3, 2005.

* cited by examiner

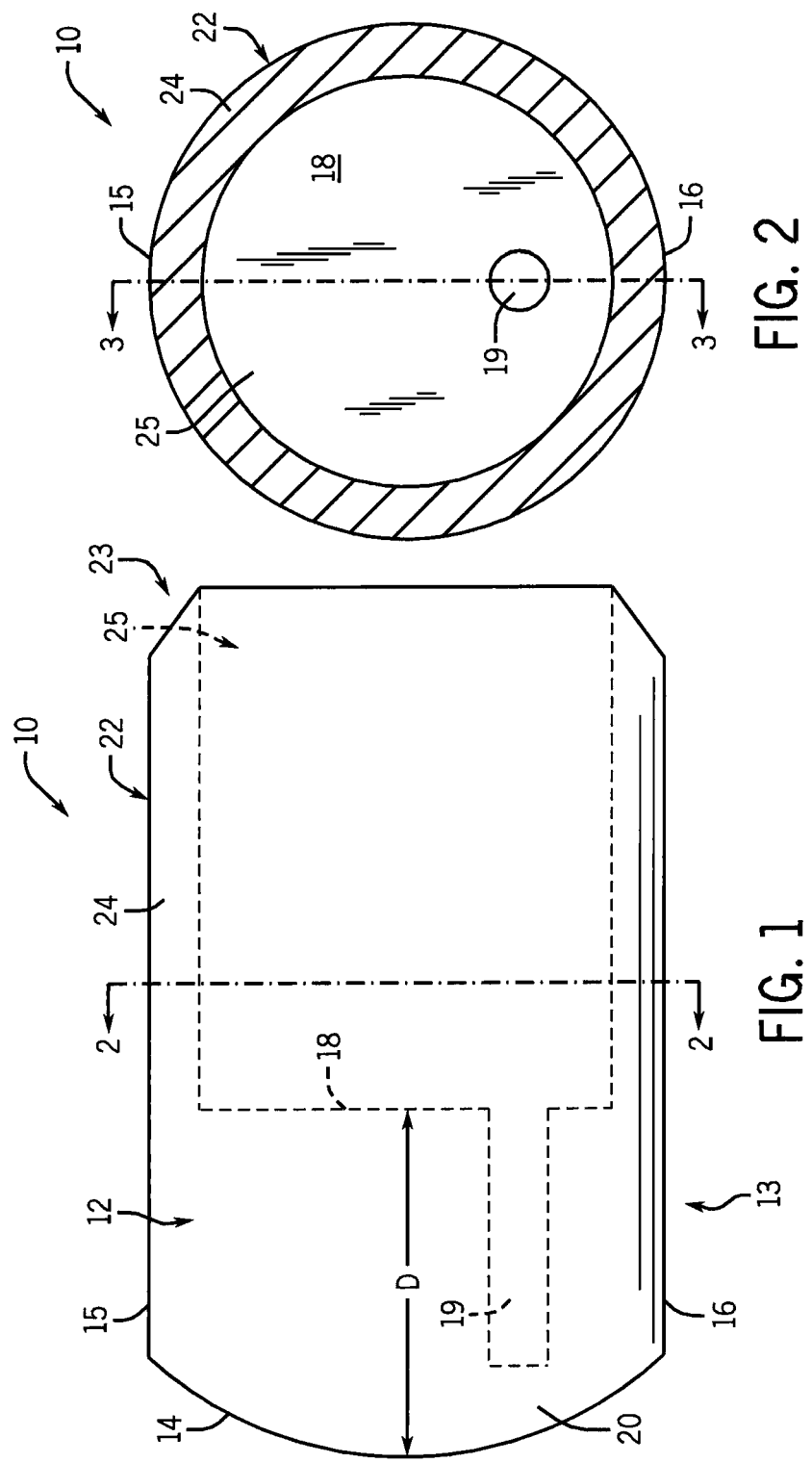

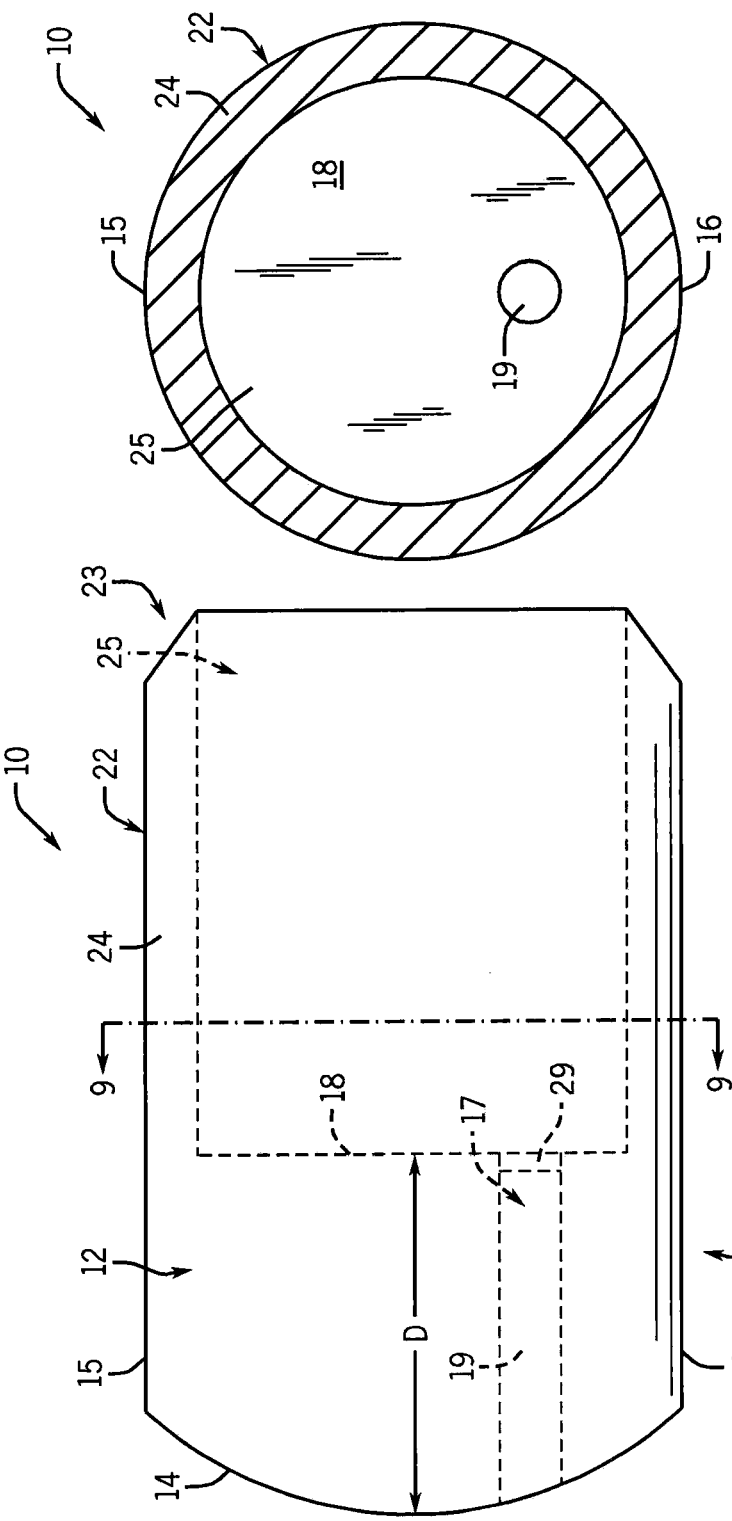

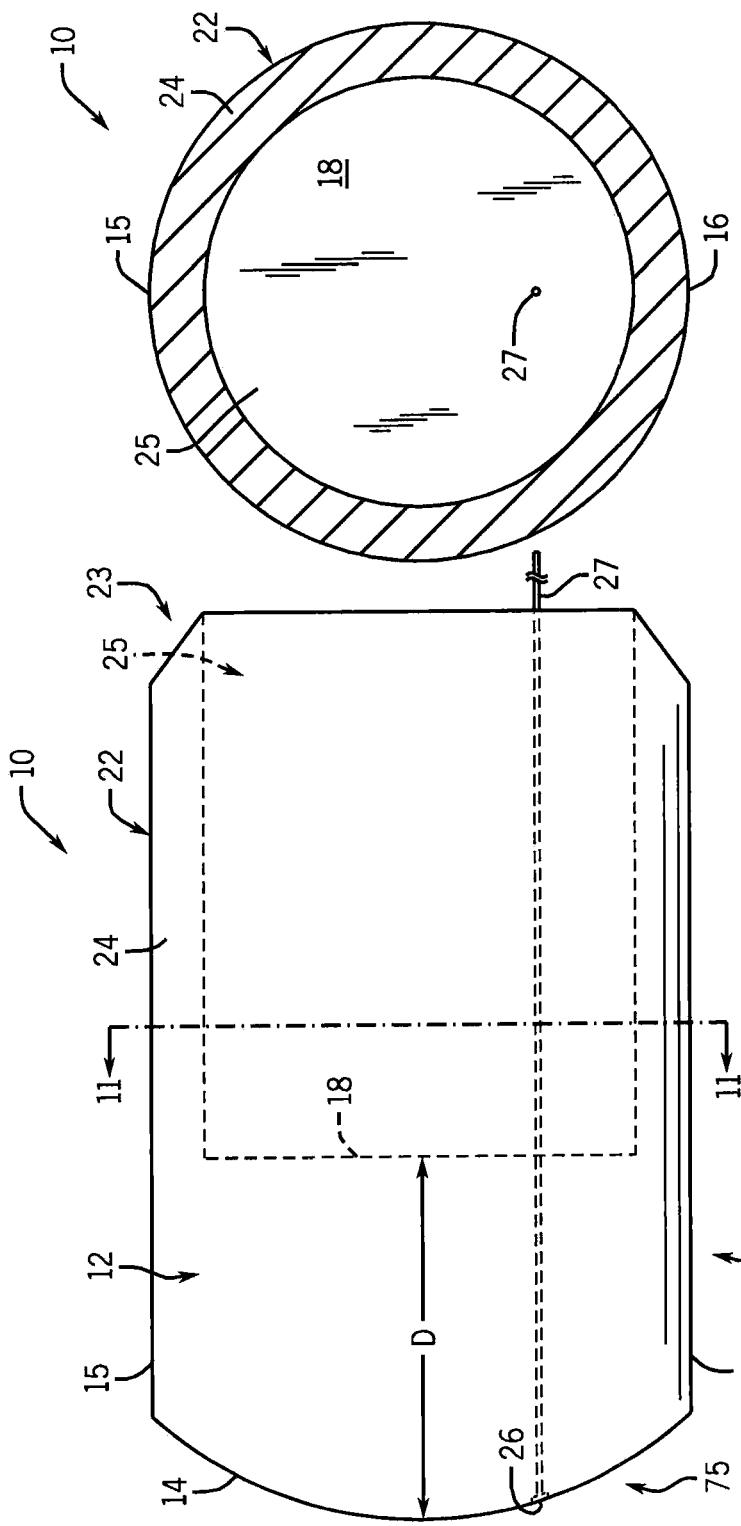

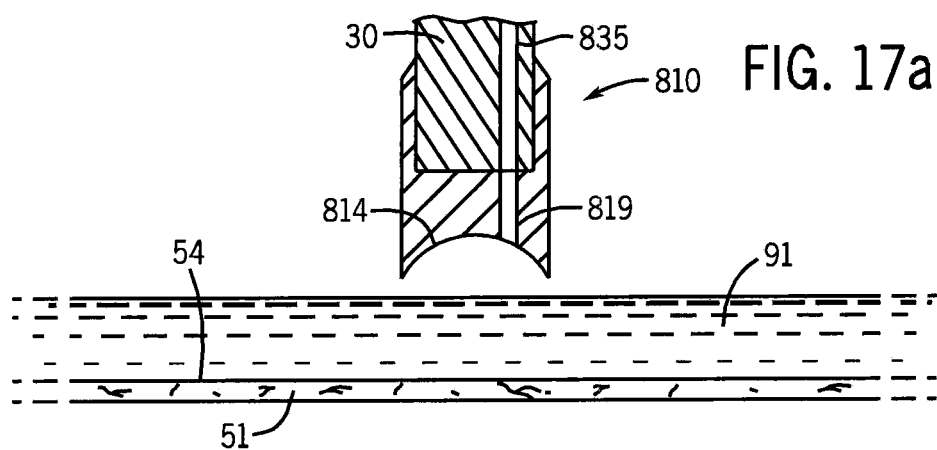
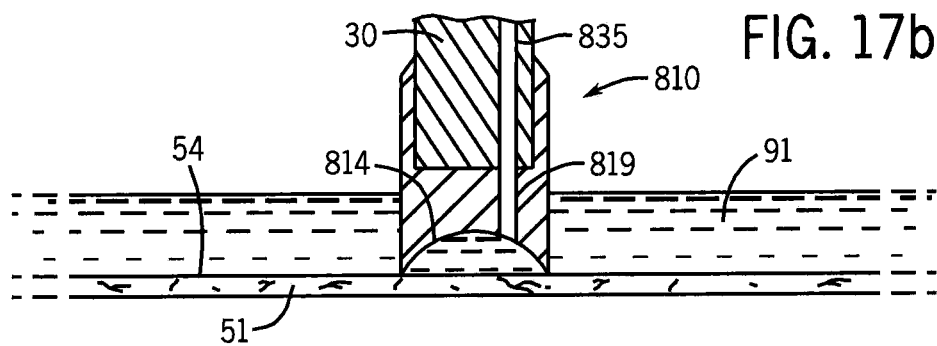
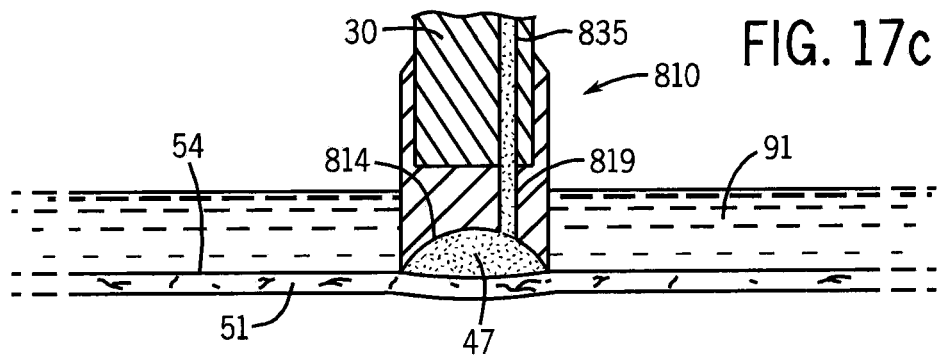

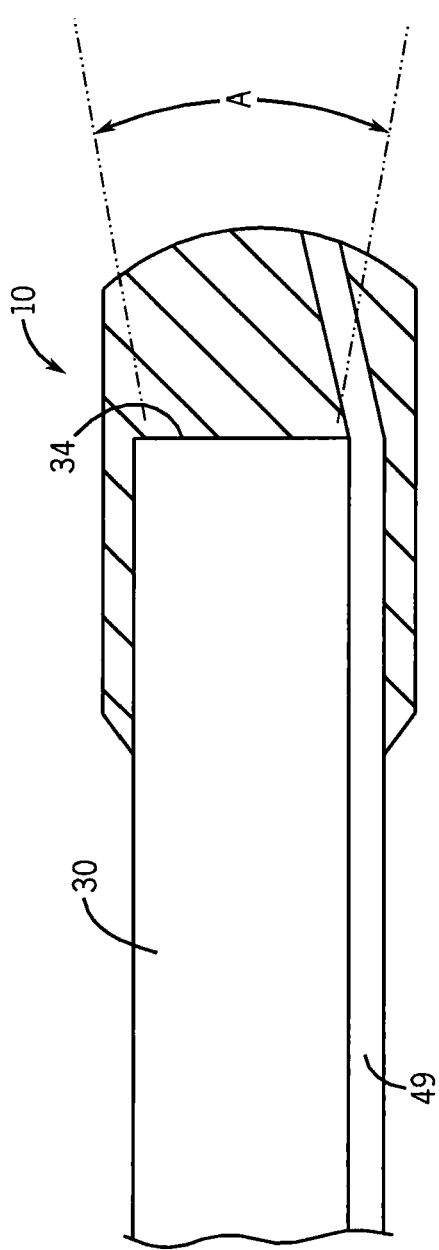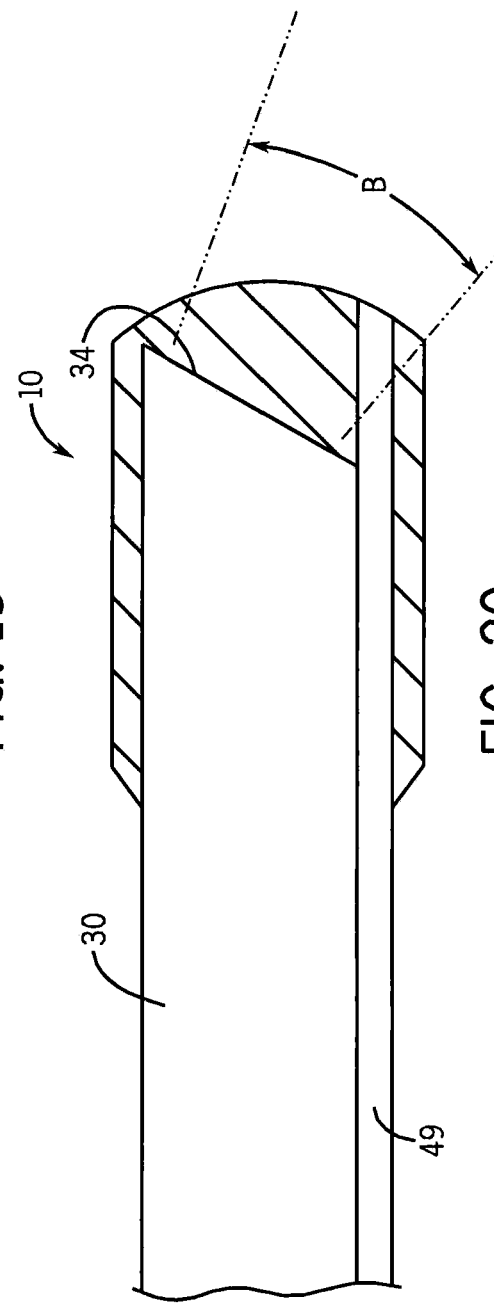
FIG. 19
FIG. 20

OPTICAL COUPLER FOR AN ENDOSCOPE

CROSS-REFERENCES TO RELATED APPLICATIONS

This application claims priority to U.S. Provisional Patent Application No. 61/443,546 filed Feb. 16, 2011, which is hereby incorporated by reference as if set forth in its entirety.

STATEMENT REGARDING FEDERALLY SPONSORED RESEARCH

Not Applicable.

BACKGROUND OF THE INVENTION

1. Field of the Invention

This invention relates to an optical coupler for improved optical imaging of surfaces covered with opaque fluids, semi-solid materials or particulate matter.

2. Description of the Related Art

The demand for minimally invasive surgery continues to grow. The ability to convert open surgeries to minimally invasive procedures has been made possible with video endoscopy, but is limited when blood or other fluids are in the field of view. Other technologies (fluoroscopy, 3-D echo, MRI, etc.) currently are used to overcome the challenge of performing surgery in intravascular spaces, but each technology presents limitations.

Fluoroscopy has a two dimensional view and is used for diagnostic procedures or placement, and/or deployment of medical devices. Procedures are lengthy creating increased exposure to radiation for both patients and clinicians, increased expense, and also may increase morbidity due to extended anesthesia duration. Most importantly, images are inferior to direct vision, the gold standard in surgery.

Ultrasound three dimensional imaging systems have known problems as well. Images are created by transforming ultrasound waves to images. Images often contain shadowing or ghosting when instruments or devices are placed within the viewing field. MRI surgical procedures are very limited, costly and complex. Simple procedures take hours.

What is needed therefore is a device that allows diagnostic and surgical procedures to be performed in areas of the body where visibility is normally or has been obstructed by blood, stomach content, bowel content, or other opaque fluids and/or solid particulate matter.

SUMMARY OF THE INVENTION

The foregoing needs are met by an optical coupler comprising a clear gel in a semi-solid state that attaches to the distal end (objective lens) of a conventional or modified video endoscope for performing diagnostic procedures and/or minimally invasive surgical operations. The optical coupler is biocompatible and for single use. It can be attached to rigid or flexible endoscopes (for example, gastroscopes thorascopes, laparoscopes, colonoscopes, Natural Orifice Transluminal Endoscopic Surgery (NOTES) endoscopes, esophagoscopes, nasolarynoscopes, arthroscopic scopes and ophthalmoscopes used in laparoscopic, gastrointestinal, thorascopic, colonoscopy and other endoscopic procedures). The optical coupler is an important advancement in minimally invasive surgeries and as a tool utilized in diagnosis and treatment of disease.

The optical coupler of the invention is used for visualization in opaque fluids or semisolids, and comprises a clear, soft, flexible gel coupled to the outer distal portion of any optical imaging device, such as an endoscope or a camera lens. When pressed in contact with the surface of an area to be viewed, the coupler creates an offset that allows clear visualization by mechanically displacing the opaque liquid, semi-solids, or particulate matter. This displacement allows the optically clear coupler to come into contact with a surface of interest, thus producing an unobstructed view to the observer.

In a non-limiting medical embodiment, the coupler solves a long-standing medical challenge: keeping the tissue undergoing diagnostic or surgical repair free of blood, bile, and/or other opaque fluids that would obstruct the clinician's view. Because the coupler comprises a clear soft elastic gel, standard medical instruments can be maneuvered within the area of the offset, giving the clinician seamless access and a clear view of tissue in situ. The coupler provides for reduced surgical procedure time resulting in less invasive effects and quicker patient recovery, and potentially higher volume of scheduled procedures. The coupler is intuitive to use and would not require any learning curve for the clinician.

In a non-limiting industrial embodiment, the coupler can be attached to a borescope, pipe inspection or other imaging equipment to evaluate or repair surfaces obstructed by opaque fluids or solutions, semisolids, or particulate matter, such as oil, sewage or silt.

In one aspect, the invention provides an optical coupler for mounting at a distal end of an optical imaging device for visualizing a surface area covered with an opaque fluid and/or particulate matter. The coupler includes a visualization section at one end of the coupler and an attachment section connected to and extending away from the visualization section. The attachment section is dimensioned to be mounted at the distal end of the optical imaging device. The visualization section includes a proximal surface for engaging the distal end of the optical imaging device. The visualization section includes an outer surface spaced apart from the proximal surface. The outer surface extends continuously from a first outer side boundary across to a second opposite outer side boundary of the visualization section. The visualization section may include a hollow instrument channel extending from the proximal surface toward or through the outer surface. The visualization section can be formed from an elastic material capable of transmitting an optical image of the surface area. In one form, the material comprises a silicone gel or a silicone elastomer.

In another aspect, the invention provides a device for visualizing a surface area covered with an opaque fluid and/or particulate matter. The device includes a sheath having a first lumen and a second lumen, a light guide positioned in the first lumen for transmitting light toward the surface area, an image carrying fiber positioned in the second lumen, an object lens positioned at a distal end of the image carrying fiber and optically connected to the image carrying fiber wherein the lens receives light that has been reflected from the surface area, and an optical coupler mounted at a distal end of the sheath. The coupler includes a visualization section at one end of the coupler. The visualization section includes a proximal surface for engaging the distal end of the optical imaging device, and the visualization section includes an outer surface spaced apart from the proximal surface wherein the outer surface extends continuously from a first outer side boundary across to a second opposite outer side boundary of the visualization section. The visualization section includes a hollow instrument channel extending from the proximal surface toward the outer surface. The visualization section can comprise an elastic material capable of transmitting an optical image of the surface area. The coupler includes an attachment section connected to and extending away from the visualization section wherein the attachment section is dimensioned to be mounted at the distal end of the optical imaging device.

In yet another aspect, the invention provides a method for visualizing a wall defining a body cavity with an endoscope wherein the wall is covered or obstructed with an opaque fluid and/or particulate matter. The method uses an endoscope comprising a sheath having a first lumen and a second lumen, a light guide positioned in the first lumen, an image carrying fiber positioned in the second lumen, and an object lens positioned at a distal end of the image carrying fiber wherein the lens is optically connected to the image carrying fiber. An optical coupler is mounted on a distal end of the sheath. The coupler includes a visualization section at one end of the coupler. The visualization section includes a proximal transverse surface engaging the distal end of the sheath. The visualization section includes an outer surface spaced apart from the proximal surface wherein the outer surface extends continuously from a first outer side boundary across to a second opposite outer side boundary of the visualization section, and the visualization section comprises an elastic material capable of transmitting an image of the surface area. The endoscope is inserted into the body cavity, and the optical coupler is positioned in contact with a region of the wall of the body cavity thereby displacing opaque fluid and/or particulate matter adjacent the region. Light is transmitted through the light guide and optical coupler onto the region, and light that has been reflected from the region is received at the lens and an optical image is transmitted from the lens to the image carrying fiber. In still another aspect, the invention provides a method for visualizing a wall defining a body cavity with an endoscope where the wall is covered with an opaque fluid and/or particulate matter. The method includes the steps of: (a) providing an endoscope comprising (i) a sheath having a first lumen, a second lumen, a third lumen and a fourth lumen, (ii) a light guide positioned in the first lumen, (iii) an image carrying fiber positioned in the second lumen, and (iv) an object lens positioned at a distal end of the image carrying fiber wherein the lens is optically connected to the image carrying fiber; (b) inserting the endoscope into the body cavity; (c) feeding a first precursor through the third lumen and feeding a second precursor through the fourth lumen such that the first precursor and the second precursor react to form an optical coupler on a distal end of the sheath. The first precursor can be an optical fluid and the second precursor can be a cross linking agent.

The coupler includes a visualization section at one end of the coupler. The visualization section includes a proximal transverse surface engaging the distal end of the sheath, and the visualization section includes an outer surface spaced apart from the proximal surface. The outer surface extends continuously from a first outer side boundary across to a second opposite outer side boundary of the visualization section, and the visualization section comprises an elastic material capable of transmitting an image of the surface area. The optical coupler is positioned in contact with a region of the wall of the body cavity thereby displacing opaque fluid and/or particulate matter adjacent the region. Light is transmitted through the light guide and optical coupler onto the region, and light that has been reflected from the region is received at the lens and an optical image is transmitted from the lens to the image carrying fiber.

In still another aspect, the invention provides for a method for visualizing a surface of a structure with a camera, the surface being covered with an opaque fluid and/or particulate matter. The method includes (a) providing a camera having a lens and a source of light and (b) mounting an optical coupler on the camera by engaging the optical coupler on an outer surface of the camera, the coupler including a visualization section at one end of the coupler, the outer surface extending continuously from a first outer side boundary across to a second opposite outer side boundary of the visualization section, and the visualization section comprising an elastic material capable of transmitting an image of the surface area. The method also includes (c) placing the camera and the optical coupler near the surface of the structure, (d) positioning the optical coupler in contact with a region of the surface of the structure thereby displacing opaque fluid and/or particulate matter adjacent the region, (e) transmitting light from the light source through the optical coupler onto the region, and (f) receiving at the lens, light that has been reflected from the region and capturing an optical image on the camera.

In yet another aspect, the invention provides for a method for visualizing a surface of a structure with a borescope, the surface being covered with an opaque fluid and/or particulate matter. The method includes (a) providing a borescope comprising (i) a sheath having a first lumen, a second lumen a third lumen and a fourth lumen, (ii) a light guide positioned in the first lumen, (iii) an image carrying fiber positioned in the second lumen, and (iv) an object lens positioned at a distal end of the image carrying fiber, the lens being optically connected to the image carrying fiber; (b) placing the borescope near the surface; and (c) feeding a first precursor through the third lumen and feeding a second precursor through the fourth lumen such that the first precursor and the second precursor react to form an optical coupler on a distal end of the sheath, the coupler including a visualization section at one end of the coupler, the visualization section including a proximal transverse surface engaging the distal end of the sheath, the visualization section including an outer surface spaced apart from the proximal surface, the outer surface extending continuously from a first outer side boundary across to a second opposite outer side boundary of the visualization section, and the visualization section comprising an elastic material capable of transmitting an image of the surface area. The method also includes (d) positioning the optical coupler in contact with a region of the surface of the structure thereby displacing opaque fluid and/or particulate matter adjacent the region; (e) transmitting light through the light guide and optical coupler onto the region; and (f) receiving at the lens, light that has been reflected from the region and transmitting an optical image from the lens to the image carrying fiber.

In yet another aspect, the invention provides for a handheld device that includes a handle providing a user a portion to grip and a frame connected to the handle. The frame has a cavity. A transparent section is held within the cavity, the transparent section can be punctured.

These and other features, aspects, and advantages of the present invention will become better understood upon consideration of the following detailed description, drawings and appended claims.

BRIEF DESCRIPTION OF THE DRAWINGS

FIG. 1 is a side view of a first embodiment of an optical coupler according to the invention.

FIG. 2 is a cross-sectional view of the optical coupler of FIG. 1 taken along line 2-2 of FIG. 1.

FIG. 8 is a side view of another embodiment of an optical coupler according to the invention similar to the coupler in FIGS. 1 and 2, but with the instrument channel extended through the outer surface.

FIG. 9 is a cross-sectional view of the optical coupler of FIG. 8 taken along line 9-9 of FIG. 8.

FIG. 10 is a side view of another embodiment of an optical coupler according to the invention where there is not an instrument channel in the coupler, and an electrode and wire are molded into the coupler.

FIG. 11 is a cross-sectional view of the optical coupler of FIG. 10 taken along line 11-11 of FIG. 10.

FIG. 12d is a detailed view of the embodiment shown in FIG. 12a.

FIG. 17a is a cross-sectional view of a coupler having a concave outer surface that is attached to an endoscope approaching tissue covered in blood.

FIG. 17b is a cross-sectional view of the coupler and endoscope from FIG. 17a, with the coupler pressed against a wall.

FIG. 17c is the cross-sectional view of the coupler and endoscope from FIG. 17b, with fluid from the instrument channel flushing the trapped opaque liquid between the outer surface of the coupler and the wall.

FIG. 18b is an exploded view of the coupler of FIG. 18a.

FIG. 19 is a coupler attached to a rigid endoscope having a 0° end surface, with the coupler having an angled instrument channel.

FIG. 20 is a coupler attached to a rigid endoscope having a 30° end surface, with the coupler having a straight instrument channel.

FIG. 23b is an exploded view of the mold of FIG. 23a.

Like reference numerals will be used to refer to like parts from Figure to Figure in the following description of the drawings.

DETAILED DESCRIPTION OF THE INVENTION

Figure 3:
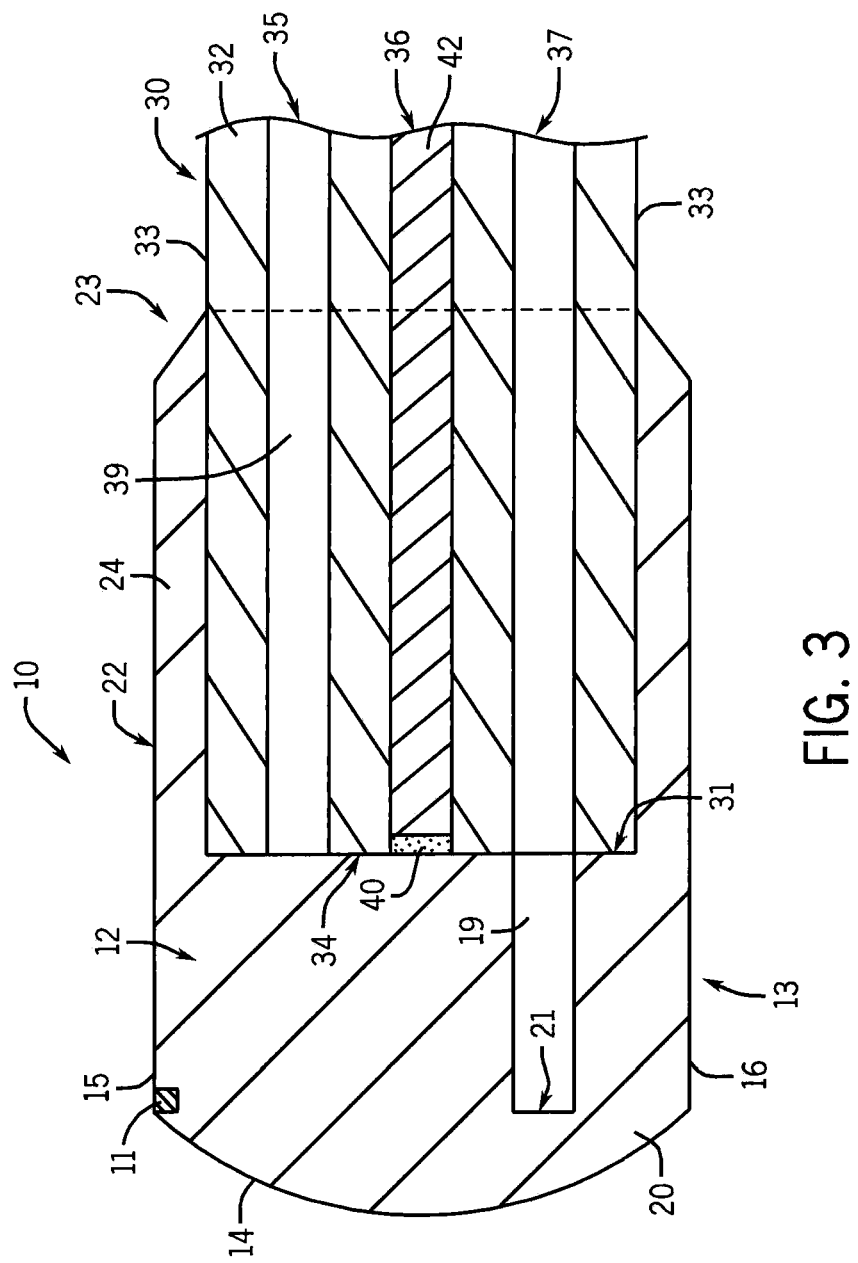
FIG. 3 is a cross-sectional view of the optical coupler of FIGS. 1 and 2 taken along line 3-3 of FIG. 2, the optical coupler being attached to an endoscope.

The invention provides an optical coupler for improved optical imaging of surfaces covered with opaque fluids, semi-solid materials or particulate matter. In one form, the optical coupler is a clear gel attached to the outer distal portion of any optical imaging or image capturing device, such as an endoscope or camera lens. When pressed in contact with the surface of an area to be viewed, the gel creates an offset that allows clear visualization by mechanically displacing the opaque liquid or soft semisolids.

An attachment section of the optical coupler can be mounted on the distal portion of the insertion part of the endoscope. A visualization section of the optical coupler comprises a soft, elastic, flexible, optically clear gel, and covers the distal end of the endoscope. The visualization section of the optical coupler may be thicker if a wider field of view is needed, or thinner if a closer working distance is needed. The attachment section of the optical coupler can be a sleeve continuous to the visualization section of the optical coupler. This sleeve is slipped over the distal portion of the endoscope until the inner surface of the attachment section of the optical coupler makes contact with a lens of the endoscope. The elastic properties of the sleeve-like attachment section of the optical coupler, and its smaller internal diameter provide a secure hold on the endoscope.

The optical coupler may have a hollow instrument channel or channels that extend through the visualization section of the optical coupler. The channel(s) can be the same diameter and align with the working instrument lumen(s) or channels(s) of the endoscope. This allows probes or instruments to be passed from the endoscope lumens or channels through the visualization section of the optical coupler.

Often during endoscopic examinations and procedures, the tissue or an object being viewed is or can be obstructed by blood or other opaque bodily fluids. With the optical coupler attached to the endoscope, the optical coupler pushes through the opaque fluid, displacing it. Since the coupler is soft, contact can be safely made with the tissue or object needed to be viewed. The optical coupler, with slight compression, will keep in contact with the tissue and because the visualization section of the optical coupler is clear, visibility is not impeded thereby providing a clear view to image with the endoscope.

The object being viewed may have steep undulations. In one embodiment of the coupler, a very low durometer (soft) surface of the coupler conforms to the shape of the object. The coupler has a very elastic nature so vibrations and movements of the endoscope are dampened, also improving the ability to visualize. The optical coupler's soft, flexible, elastic properties will cause minimal deformation or damage to soft tissue. Additional force beyond what is needed to displace the opaque fluid can be applied to the endoscope to flatten or unfold tissue that may be in a contracted state. This would reveal areas of the tissue that would not be seen without the coupler. In another embodiment, the coupler can be comprised of a high durometer (stiff) material to allow the tissue to conform to the shape of the coupler. Because the tissue conforms to the shape of the coupler, fluids are displaced and allow clear visualization. In both embodiments, medical instruments can be passed through the aligned working instrument lumen(s) of the endoscope and instrument channel(s) of the coupler, making surgical repairs, taking biopsies, etc., possible with endoscopic instruments and methods.

Depending on the endoscopic procedure, the optical coupler properties may vary. For example, a high tensile strength and high tear resistance for the coupler material may be suitable. In certain applications, a totally elastic material that provides an elastomeric coupler may be beneficial.

Couplers composed of hydrophobic materials may be the best choice for use in a water or blood environment. For example, a coupler composed of silicone material repels blood, staying clear for extended periods of use, additionally the silicone repels lipids. The coupler, or a portion of the coupler, being composed of a hydrophobic substance will not swell from the uptake of water or fluids in its working environment.

In an oil, grease, and water environment, a coupler coated with a super hydrophilic would be advantageous. After the coupler has an initial exposure to water, water molecules push away other molecules, gaining access to the surface of the coupler forming stable hydrogen bonds that are reluctant to break. This keeps contaminants away from the coupler so it remains clear longer.

Couplers composed of hydrophilic materials may be advantageous in the coupler. If the coupler or portions of the coupler are composed of a hydrophilic substance, it will swell in its working environment increasing the area of displacement or swell to a predetermined shape.

High thermal resistance can be beneficial in the material of the coupler. For example, the material will not melt with heat (e.g., 500° F.-1200° F.) from electrocautery or radio ablation procedures. Electrical isolative, high corona resistance materials are also beneficial when the coupler is used in electro, radio frequency, cautery, or harmonic scalpel procedures.

The coupler also provides for various safety improvements in endoscopic procedures. In both laparoscopic and general surgery, smoke emitted from the burning tissue while using electro cauterization instruments often cause poor or zero visibility in the surgical field. The procedures must be stopped until the smoke is dissipated. When the electro cauterization is used in conjunction with the coupler constant visualization of the tissue remains, the coupler displaces the smoke. The coupler can be dimensioned so that it is soft with no sharp edges to cause dissections. The coupler can be dimensioned with a larger surface area to dissipate force when an endoscope is pushed forward in a body lumen. The coupler is dimensioned with a large outer surface area as compared to the objective lens of the endoscope. This is advantageous as one small drop of blood can totally obscure vision from an endoscope objective lens. Small drops of blood on the outer surface of coupler will only partially obscure visibility. The coupler can be dimensioned with a domed shape, smooth slippery outer surface that will allow better maneuvering in tube-like structures such as the esophagus, colon, veins, and arteries. The coupler also corrects wide-angle curvature created by the common lens used on videoscopes.

The coupler gel can be composed with a variety of materials including polydimethylsiloxane, hydrogels, polyurethanes, albumin based gels, mineral oil based gels, polyisoprene, polybutadiene, or other clear composite. One preferred material is polydimethylsiloxane because of its biocompatibility in medical applications, low price, and it is easy to mold and cure. Clear, flexible hydrogels that have extreme resistance to tearing are another preferred material.

The material used to form the optical coupler can be comprised of two or more compounds, for example an opaque compound attaches and holds two visualization portions of a coupler in position, the first visualization portion is an inner clear semi rigid compound shaped to match the field of view and minimum depth field of the imaging system, and the second portion is attached to the outer boundary of the first visualization portion and is composed of very soft gel providing additional area of fluid displacement for maneuvering and positioning instruments under direct vision. Methods described in U.S. Pat. Nos. 7,235,592 and 7,205,339 can be utilized to produce a coupler with portions or areas of the gel with different physical properties.

The invention can be used in various applications. With Natural Orifice Translumenal Endoscopic Surgery (NOTES), the coupler enables procedures to continue when unexpected bleeding or other fluids such as bile or stomach contents obstruct the view. Also, the coupler can create or increase working space by pushing organs out of the field of view. With a laryngoscope in trauma and emergency situations, the coupler would push blood, foreign objects, or food away to increase visibility to allow visualizing of the trachea. When taking biopsies is required, the coupler isolates the intended biopsy target, the tumor or area to be biopsied from surrounding tissue. Close focusing and contact with the tissue with the aid of the coupler can improve reliability by allow multiple biopsies to taken in exact locations defining borders of the tumor, and minimize tumor cells from entering the blood stream or lymph channels. A cautery probe or electrode can be used simultaneously or in conjunction with the biopsy forceps, minimizing bleeding and length of procedure.

The coupler can be used in various endoscopic intra-cardiac procedures such as: (1) myocardial biopsy (for transplant monitoring or tumor sampling); (2) valve repair or reconstruction; (3) patent foramen ovale (PFO) closure; (4) ventricle septal defect (VSD) closure; (5) pacing wire placement or removal; (6) stem cell injection; (7) coronary sinus cannulations (8) and maze procedure. In cryoablation, a specialized composite coupler could be made that has warming channels to warm the external surface of the coupler to protect surrounding tissue from freezing. In radiofrequency ablation, insulating and isolating properties of the coupler would concentrate power, protecting surrounding tissue.

The coupler can be used in various vascular procedures. The coupler can be used to guide proper placement of covered stents in dissected aortas, or visualize an intra-vascular laser. The coupler could be used to inspect the suture line of a large or small vessel anastomosis to evaluate the quality of the suturing and or determine the location of any bleeding.

In certain surgical or trauma situations there is severe arterial bleeding from a wound or vessel. Often the first action taken is to compress a finger or sponge on the area of bleeding. After time passes the finger or sponge is removed. If the bleeding continues either more compression or other actions are taken such as blind clamping, suctioning the blood away and then clamping and suturing, or homeostatic materials are applied. Blood loss can be substantial. An embodiment of the invention mounted at the end of a finger shaped wand can be compressed over a bleeding site, both clearing the field of blood and creating a view to locate the point of bleeding. Since the coupler is clear, soft and biocompatible, a suture or staple can be passed though the coupler to repair the bleeding site.

The coupler is also beneficial in non-medical applications. Embodiments of the coupler can be attached to the distal end (objective lens) of a borescope or attached to micro or conventional video cameras, inspection scopes, or still cameras. This allows viewing and/or making repairs inside pipes, holding tanks, containers, etc when the fluid is opaque, such as petroleum products, sewerage, food products, paint, etc, eliminating the need to empty the pipes or containers (e.g., oil tanks). The size of the coupler or the amount of flexibility can be scaled for specific applications, for example, displacing large volumes of fluid when examining large areas. The shape of the coupler can be generally flat, convex (with varying levels of curvature), or shaped for specific tasks. For example, the coupler may be shaped as a square, or as an angular shape to displace opaque fluids in the corners of a tank to inspect the seams. Examination of joints, welds, seams for corrosion or cracks could be performed in pipes that contain moving fluid. A coupler could be used in conjunction with a video camera and a robotic vehicle to view remote locations. Large couplers with large working channels will allow devices to be passed though a coupler to make repairs using screws, adhesive patches, etc. The coupler can be formed from materials that resist acid, alkalinity, high heat, or viscosity of the fluid being displaced by the coupler. As opposed to medical usage (disposable, single use), the coupler preferred embodiment with industrial applications would be reusable.

The working channels within the coupler or parallel to the coupler allow surgical instruments, probes, biopsy needles, needles, sutures etc. to be passed to the area being viewed. Since the coupler is flexible, the channels can move within or around the coupler without compromising its function. One enabling property of the coupler is its soft flexible shape that conforms to the tissue or object being viewed. This characteristic reduces damage to delicate tissues or structures.

Another advantage of the coupler is that only the specific area being viewed through the coupler attached to the endoscope requires illumination and therefore, the targeted view requires less light to be supplied by the endoscope lighting system. Because the number of light fibers required for illumination is less, endoscopes can be smaller or less expensive to manufacture. Also, since it is only necessary to illuminate the area of the coupler at its outer boundary, endoscopes of smaller diameter would be required to view a targeted area.

An external light source for the endoscope can increase the functionality of the coupler. When the coupler does not contact the surface of tissue in a large chamber, such as the stomach inflated with air, light emitting from the distal end of the endoscope can be reflected from the outer surface of the coupler back to the camera lens, degrading the endoscope view. Using an external light source and turning off the endoscope light source reduces the reflection. Alternatively, a light fiber placed through the instrument channel which stops at the outer boundary will provide lighting while viewing objects in the inflated stomach. After the coupler contacts the tissue covered by opaque fluid or blood, the external light is shut off or the light fiber is withdrawn from the instrument channel.

The coupler can be a semi-solid gel, which is transparent and flexible, that attaches to a wide variety of endoscopes. For minimally invasive procedures, the smallest possible scope is used. The optimal shape and size of the coupler can be determined by the field of view of the endoscope, or conversely an endoscope can be chosen that will match the size and shape of the coupler. The shape of the coupler can be manufactured with a preformed shape matched to the contour of the object that will be examined, for example an endoscope coupler could be made in the shape of the blood pool at the apex of the heart. This coupler can be used in conjunction with a 2 mm angioscope maneuvered into the apex of the heart and displace the blood to visualize the inside wall of the ventricle of the beating heart.

The coupler can be attached to the endoscope with a clear adhesive material. The coupler can be attached as a screw on auxiliary lens or filter allowing different couplers with different purposes or functions to be utilized with the same scope. The coupler can be attached and held in place with suction. The coupler can be attached by sewing on with sutures. The coupler can be attached with wire, nylon or other braid material. The coupler can be attached to endoscopes with mesh or pliable membranes. When using a mesh net to attach the coupler to the endoscope, gel strength and viscosity must be high enough to prohibit gel flow through holes in the outer layer of mesh.

A coupler can be compressed in a tube fixed to the end of the scope. A coupler attached to the endoscope can be compressed in a retractable sheath.

The coupler can be made in situ by injecting an optical fluid (e.g., a siloxane polymer) and a cross linking agent (e.g., a multifunctional silane) into two separate lumens of the endoscope. The liquid components combine and crosslink to form a cured viscoelastic solid (e.g., a silicone gel or silicone elastomer) inside a pliable membrane attached to the distal end of the scope. The solid body of the coupler can be reinforced with micro thin strands of biocompatible fibers, carbon fiber, Nitinol, suture materials, and/or light fibers. In situ formation of the coupler allows a larger coupler to be formed inside the body, increasing the area of visibility. The coupler can be chemically or mechanically dissolved for removal after use.

If the coupler is confined inside a balloon, membrane, mesh or a tube-like structure with higher wall tension than the systolic blood pressure, tunnels formed by moving the instruments, probes, needles or other devices within the coupler will be refilled with gel keeping the gel transparent. To keep the gel contained within the coupler would require a gel strength high enough to prohibit flow through holes made in the outer balloon, membrane or mesh by the needles or devices.

Embodiments of the coupler can have one, two or more working channels that align with the endoscope's working lumens. Other versions of the coupler allow for additional internal channels or along the edges of the device for use in more complex procedures, such as suturing.

The coupler can be used in any minimally invasive procedure. Biopsies in the body, for example, could be taken under direct view, reducing the need for $CO_2$ inflation. The coupler allows exact placement of needles and medical devices in situations where active bleeding or other bodily fluids impede visibility. The coupler can be held with pressure over an active bleeding site to stop bleeding until the suturing process, stapling, clamping or medical device placement is complete.

Other instruments or devices can be pushed through the coupler, not compromising its form or transparency. Channels are created by piercing the coupler with needles, probes or instruments and the channel will reseal as the medical instruments are withdrawn.

Attaching the coupler to endoscopes that contain working lumens, the coupler and endoscope work in unison. Transparent or semi-transparent soft flexible tubes are passed though these channels penetrating the coupler, creating continuous channels that allow probes to be passed to the targeted area. These probes may include sensors, hypodermic needles, instruments, light fibers or medical devices that can be passed in and out of the coupler to exact repeatable positions.

Fixed channels external to the endoscope can be added to steer or direct probes around the coupler to be seen and maneuvered within the viewing area. The device could be fixed to a 45 degree scope or mirror set 45 degrees to a lens to permit viewing from the side of a scope. This allows viewing of the side of vessels or tube as the scope is pushed forward. When used in conjugation with wide angle optics, the coupler yields a circumferential view in a pipe or vessel.

Turning now to FIGS. 1-3, there is shown a first example embodiment of an optical coupler 10 according to the invention. The optical coupler 10 includes a visualization section 12 at a distal end 13 of the optical coupler 10. The visualization section 12 has a generally slightly curved, convex outer surface 14 that extends from a first outer side boundary 15 to a second opposite outer side boundary 16 of the optical coupler 10. The outer surface 14 may be constructed to be generally flat, but a curved outer surface 14 is preferable because the curvature helps to clear the field of view by pushing any fluid or matter from the center of the outer surface 14 to the outer boundaries 15, 16. A flat outer surface 14 may be more difficult to clear since the pressure is equal across the entire area of contact and fluid can become trapped between the lens and a surface in which it is desired to view or perform work. A curved outer surface 14 is also preferable to correct any curvature distortion created by an objective lens 40 that may be used in conjunction with the coupler 10. The optical coupler 10 has a proximal surface 18, and a hollow instrument channel 19 extends from the proximal surface 18 toward the outer surface 14.

The hollow instrument channel 19 may be constructed such that the channel 19 does not extend all the way through the visualization section 12 to the outer surface 14. In such a case, a barrier section 20 of material is provided between a distal end 21 of the hollow instrument channel 19 and the outer surface 14 of the optical coupler 10. Alternatively, the instrument channel 19 may extend the full length of the visualization section 12, extending through the optical coupler 10, as shown in FIGS. 8 and 9. Such a configuration may allow for the free and unencumbered exchange of instruments. A water tight seal or valve 29, such as a Tuohy-Borst type valve, may be employed on the proximal end 17 of the endoscope instrument channel 19 to prevent or minimize air, fluid, and/or foreign matter from flowing through the instrument channel 19.

While an instrument channel 19 is shown in the optical coupler 10 of FIGS. 1-3, the visualization section 12 may be constructed without an instrument channel 19. In such a case, instruments may be passed directly through the visualization section 12 as the visualization section 12 may be constructed of a material that is self-sealing and elastic enough to permit instruments to be passed through the entire length of the visualization section 12 of the optical coupler 10. An example of an optical coupler 10 without an instrument channel 19 is shown in FIGS. 10 and 11, and is described in more detail below.

The optical coupler 10 also includes an attachment section 22 connected to and extending away from the visualization section 12. The attachment section 22 is at the proximal end 23 of the optical coupler 10. The proximal end 23 of the optical coupler may be angled to lessen the chance that the optical coupler 10 may catch on any surfaces when the optical coupler 10 is being removed from its environment of use. In the embodiment shown, the attachment section 22 is in the form of a cylindrical wall 24. The proximal surface 18 and the cylindrical wall 24 of the optical coupler 10 define a hollow cylindrical opening 25 of the optical coupler 10 within the sleeve-like cylindrical wall 24.

Referring to FIG. 3, the optical coupler 10 can be mounted on an endoscope 30. The endoscope 30 has a distal end 31 that is inserted in the hollow cylindrical opening 25 of the optical coupler 10. In one form, the cylindrical wall 24 of the coupler 10 has a diameter one to three millimeters larger than the endoscope 30. The endoscope 30 has a sheath 32 with an outer surface 33 that snugly engages the cylindrical wall 24 of the optical coupler 10. In a non-limiting example, the sheath 32 has an outside diameter of 7-15 millimeters. An end surface 34 of the endoscope 30 sealingly engages the proximal surface 18 of the optical coupler 10. The endoscope 30 includes a first lumen 35 and a second lumen 36 and a third lumen 37 that extend from the end surface 34 of the endoscope 30 to a proximal end (not shown) of the endoscope. Lumen internal diameters of 2-4 millimeters are typical. A light guide 39 is positioned in the first lumen 35 for transmitting light toward a surface area at or beyond the outer surface 14 of the optical coupler 10. An object lens 40 is positioned at a distal end of an image carrying fiber 42, and the lens 40 is optically connected to the image carrying fiber 42 for receiving light that has been reflected from the surface area being viewed. The object lens 40 and the image carrying fiber 42 are located in the second lumen 36. The third lumen 37 aligns with the hollow instrument channel 19 of the optical coupler 10 when the optical coupler 10 is mounted on the endoscope 30. In the embodiment shown, the instrument channel 19 and the third lumen 37 have the same size inner diameter within a tolerance of ±5%. The optical coupler 10 can also include a Light Emitting Diode (LED) 11 near the outer surface 14 of the coupler to provide illumination prior to the coupler contacting any fluids, tissue, or structure. The LED 11 may be provided power via a wire (not shown) in the endoscope 30 or from an external source.

In one example configuration, the endoscope 30 may be a fixed-focus endoscope having a specific depth of field. The outer surface 14 may be spaced apart from the proximal surface 18 of the optical coupler 10 by a length D (see FIG. 1) equal to a reference distance selected from values in the depth of field distance range of the endoscope 30. In one example configuration, the endoscope 30 may have a depth of field in the range of 2 to 100 millimeters. In this case, the outer surface 14 is spaced apart from the proximal surface 18 of the optical coupler 10 by a length in the range 2 to 100 millimeters. Preferably, the length D equals a reference distance that is in the lower 25% of values in the depth of field distance range of the endoscope 30. In one example configuration, the endoscope 30 may have a depth of field in the range of 2 to 100 millimeters. In this case, the length D equals a value of 2-26 millimeters. More preferably, the length D equals a reference distance that is in the lower 10% of values in the depth of field distance range of the endoscope 30. In one example configuration, the endoscope 30 may have a depth of field in the range of 2 to 100 millimeters. In this case, the length D equals a value of 2-13 millimeters. Most preferably, the length D equals a reference distance that is greater than or equal to the lowest value (e.g., 2 millimeters) in the depth of field distance range of the endoscope 30. In one version of the coupler 10, the length D is 7-10 millimeters, or a typical distance that the endoscope 30 is held from tissue that would be receiving an endoscopic treatment or therapy.

The design of the length D for the optical coupler 10 should also take into consideration the characteristics of the materials that compose the coupler 10, such as any possible compression of the coupler 10 when it is held against a surface. For example, if the coupler 10 may be compressed 1 millimeter when held against a surface and the lowest value in the depth of field distance range of the endoscope 30 is 2 millimeters, then the length D should be greater than or equal to 3 millimeters to compensate for this possible compression.

The optical coupler 10 can be formed from a variety of materials. In one version of the optical coupler 10, the optical coupler 10 is molded from a material selected from silicone gels, silicone elastomers, epoxies, polyurethanes, and mixtures thereof. The silicone gels can be lightly cross-linked polysiloxane (e.g., polydimethylsiloxane) fluids, where the cross-link is introduced through a multifunctional silane. The silicone elastomers can be cross-linked fluids whose three-dimensional structure is much more intricate than a gel as there is very little free fluid in the matrix. In another version of the optical coupler 10, the material is selected from hydrogels such as polyvinyl alcohol, poly(hydroxyethyl methacrylate), polyethylene glycol, poly(methacrylic acid), and mixtures thereof. The material for the optical coupler 10 may also be selected from albumin based gels, mineral oil based gels, polyisoprene, or polybutadiene. Preferably, the material is viscoelastic.

Figure 23A:
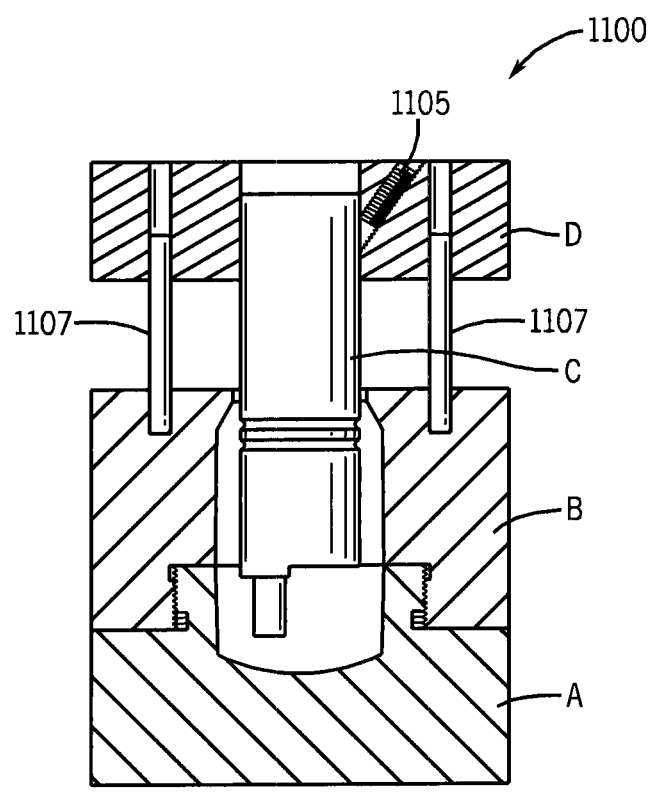
FIG. 23a is a front plan view of a mold that can be used to make a coupler.
Figure 23B:
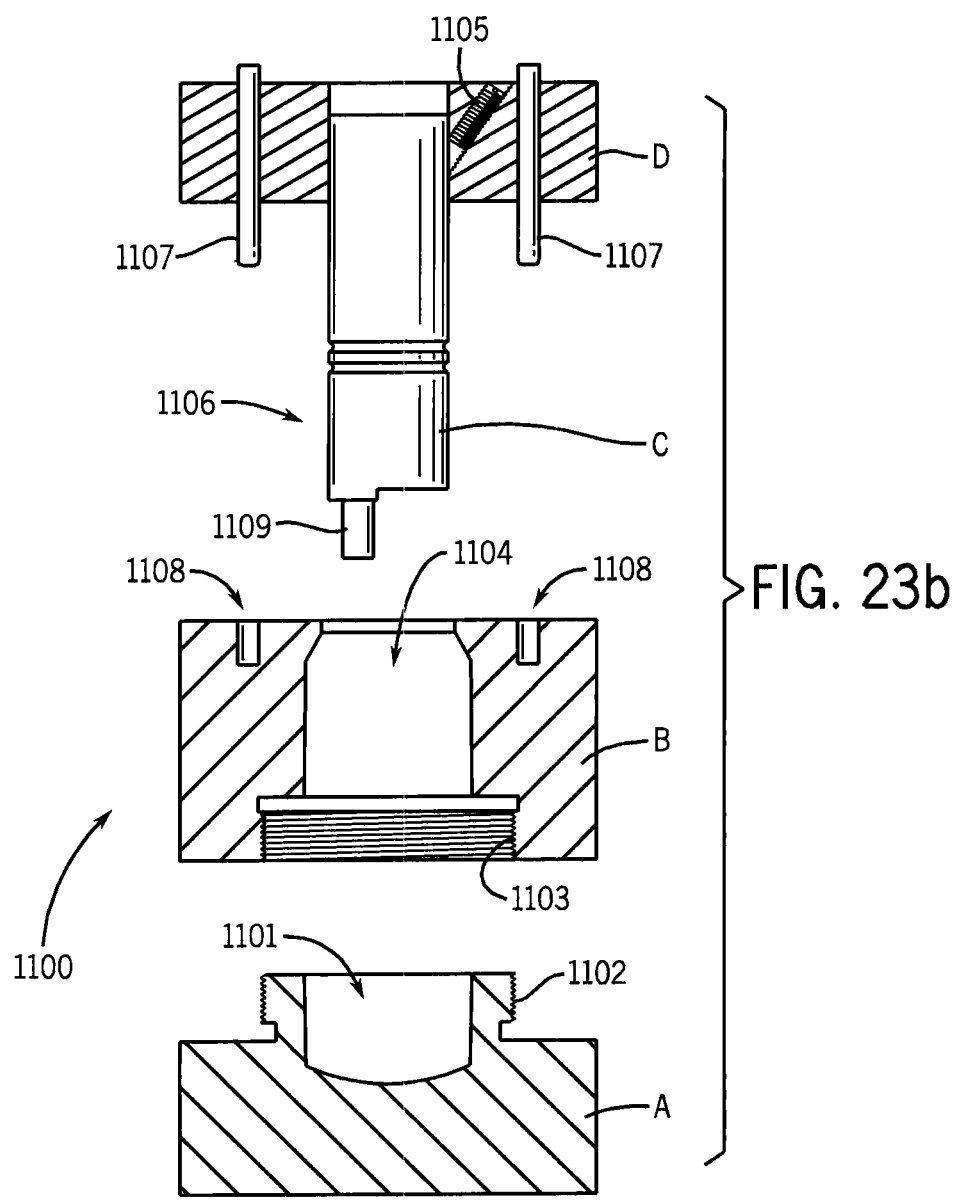

Turning now to FIGS. 23a and 23b, fully functional couplers 10 can be made by combining an uncured silicone material with an additive/heat curing agent. Various silicone material and additives can be used to produce couplers of differing degrees of softness. The material can be premixed in a 20 cc vial and placed in a vacuum chamber to remove air entrained in the silicone during the mixing process. Next, the silicone is poured into a chamber 1101 of Part A of a four piece mold 1100 and placed in the vacuum chamber if any bubbles were visible. After the silicone material in Part A was clear, Part B of the mold was screwed to Part A via threading 1102, 1103 on Parts A and B, respectively. The chamber 1104 in Part B is then filled and de-bubbled as described for part A. Mold parts C and D are pre assembled using a set screw 1105 to ensure the resulting lens have the proper shape. The leading portion 1106 of assembled Part C/D is dipped in the silicone material, then centered over the silicone in Part A/B with the aid of the alignment pins 1107 and dropped and or pushed downward in respective holes 1108 until full seated against Part B. The leading portion 1106 includes an instrument channel pin 1109 to form an instrument channel in the coupler. The assembly is cured in an oven at 90° C. for at least one hour. After curing, the mold 1100 is disassembled by unscrewing Part A from Part B, pulling Part C/D from Part B. A thick walled polyvinyl tube (not shown) can be placed over the outer surface of the coupler, after applying a vacuum to the tubing the coupler is pulled out of Part B.

Referring back to FIGS. 1-3, in the optical coupler 10, the material is optically clear such that the light guide 39 can transmit light through the optical coupler 10 toward a surface area at or beyond the outer surface 14 of the optical coupler 10 and such that the optical coupler 10 is capable of transmitting an optical image of the surface area being viewed back to the lens 40. In one version of the optical coupler 10, the material has a degree of light transmittance greater than 80% based on test standard ASTM D-1003 (Standard Test Method for Haze and Luminous Transmittance of Transparent Plastics). In another version of the optical coupler 10, the material has a degree of light transmittance greater than 90% based on test standard ASTM D-1003. In another version of the optical coupler 10, the material has a degree of light transmittance greater than 95% based on test standard ASTM D-1003. In another version of the optical coupler 10, the material has a degree of light transmittance greater than 98% based on test standard ASTM D-1003. Preferably, the material has an optical absorption of less than 0.1% in the visible light range, and more preferably the material has an optical absorption of less than 0.01% in the visible light range. The material has an index of refraction of about 1.3 to about 1.7, and preferably, the index of refraction of the material matches the index of refraction of the light guide 39, or is as low as possible.

The optical coupler 10 may also be coated with different materials to reduce the amount of adherence properties. Additionally, some coatings of the optical coupler 10 improve with light reflections. Sample coatings that may be used on the optical coupler include thermoplastic film polymer based on p-xylylene such as Parylene C, which is an optically clear biocompatible polymer having abrasion resistant and hydrophobic properties.

The hardness of the material of the optical coupler 10 can be varied depending on the application. If the surface being viewed has steep undulations, a very low durometer (soft) surface of the coupler will form to the shape of the object. Alternatively, the coupler could comprise a high durometer (stiff) material to allow the tissue to conform to the shape of the coupler. In one form, the material has a durometer ranging from 2-95 on the Shore OO scale. In another form, the material has a durometer ranging from 2-20 on the Shore OO scale. In another form, the material has a durometer ranging from 40-80 on the Shore OO scale. In another form, the material has a durometer ranging from 60-80 on the Shore OO scale. As alluded to above, the material in some applications may preferably have a durometer outside of the ranges of the Shore OO scale just discussed. Although materials having a hardness of 80 or more on the Shore OO scale may not technically be considered a "gel", this specification generally refers to the materials that can compose the coupler 10 by using the term "gel." The use of the term "gel" is not meant to limit the invention to specific materials or specific ranges of hardness on the Shore OO scale.

Figure 4:
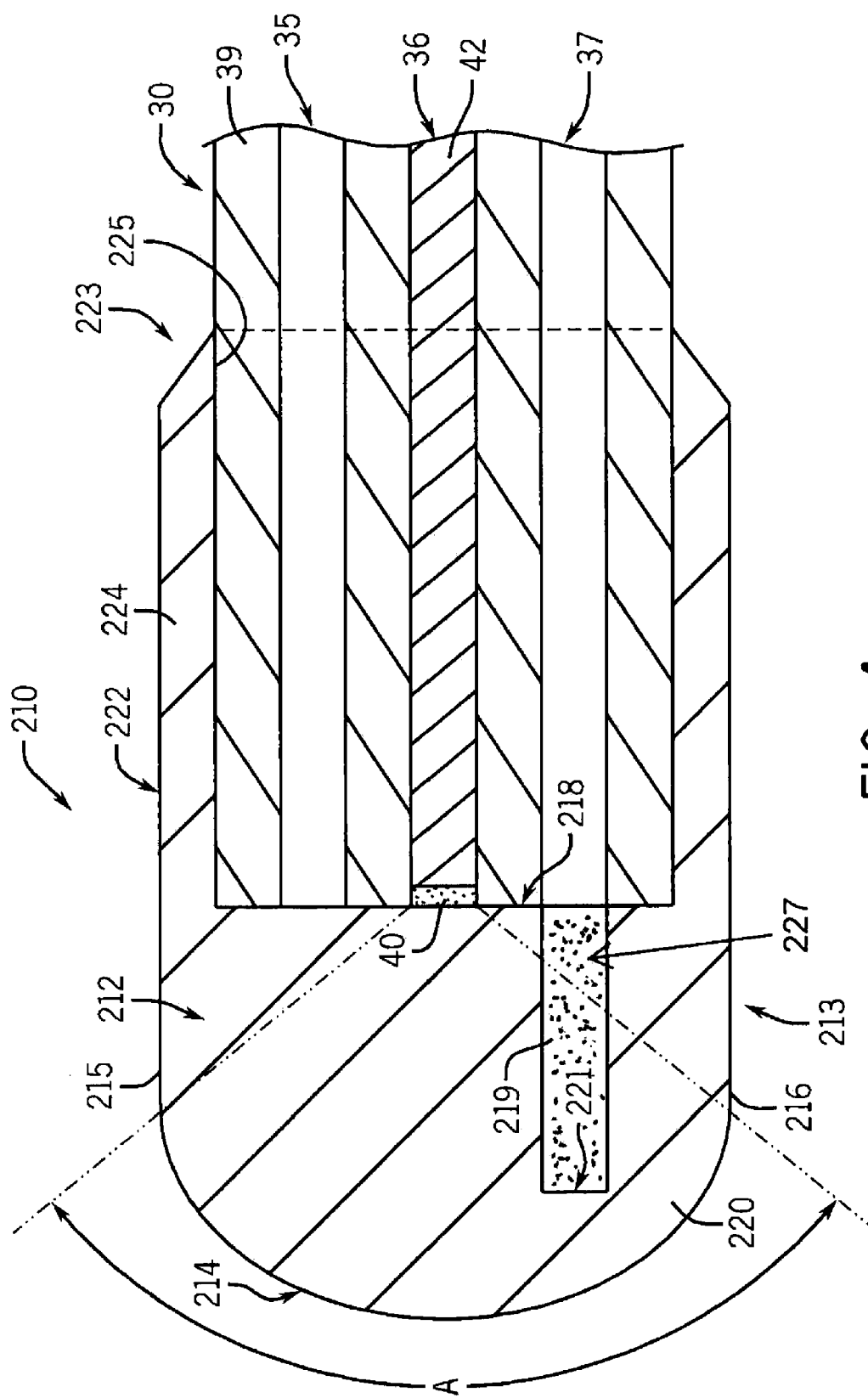
FIG. 4 is a cross-sectional view similar to FIG. 3 of a second embodiment of an optical coupler according to the invention, the optical coupler being attached to an endoscope.
Figure 5:
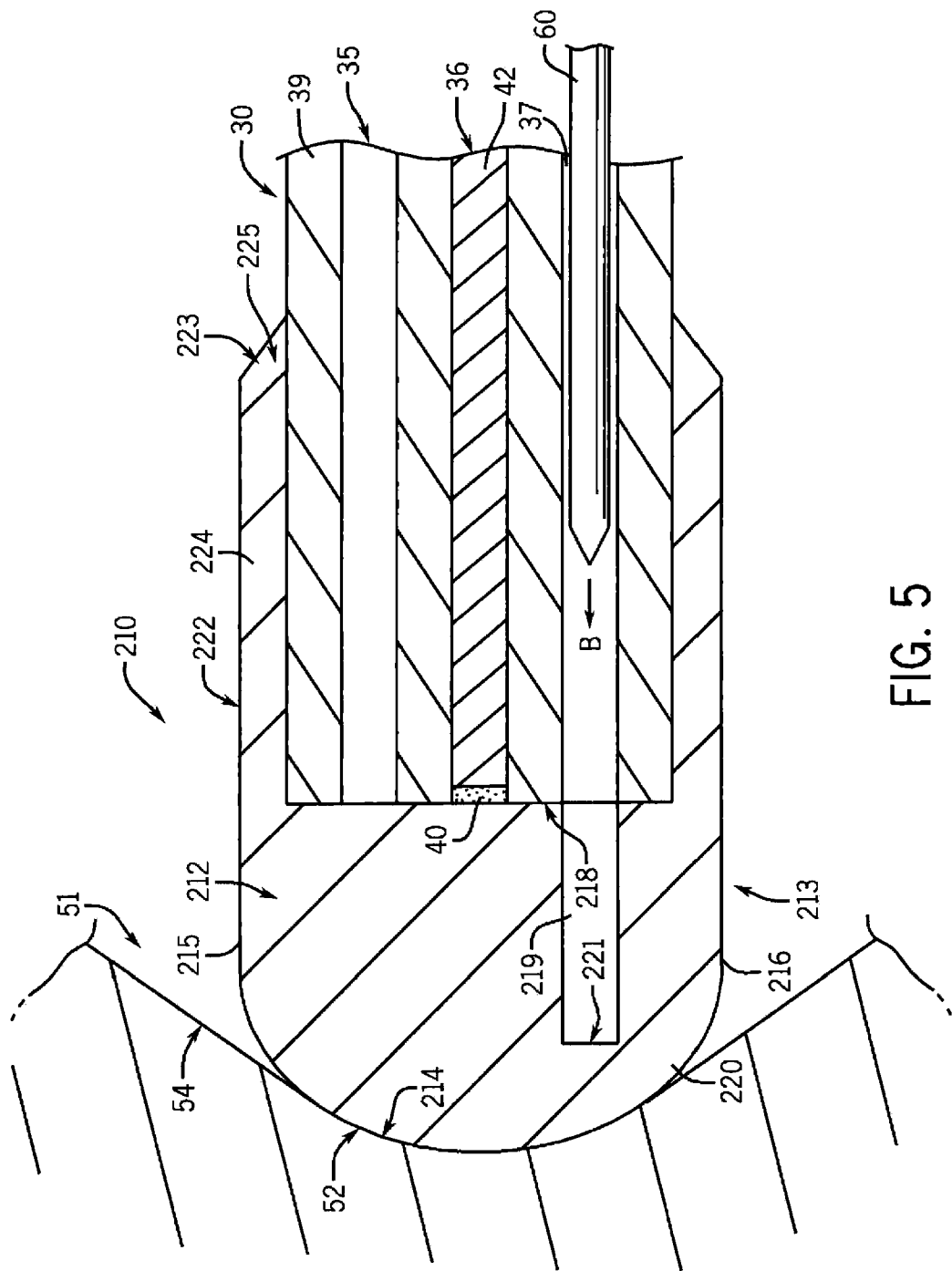
FIG. 5 is a cross-sectional view similar to FIG. 4 of the second embodiment of the optical coupler according to the invention engaging an inner wall of a body cavity.
Figure 6:
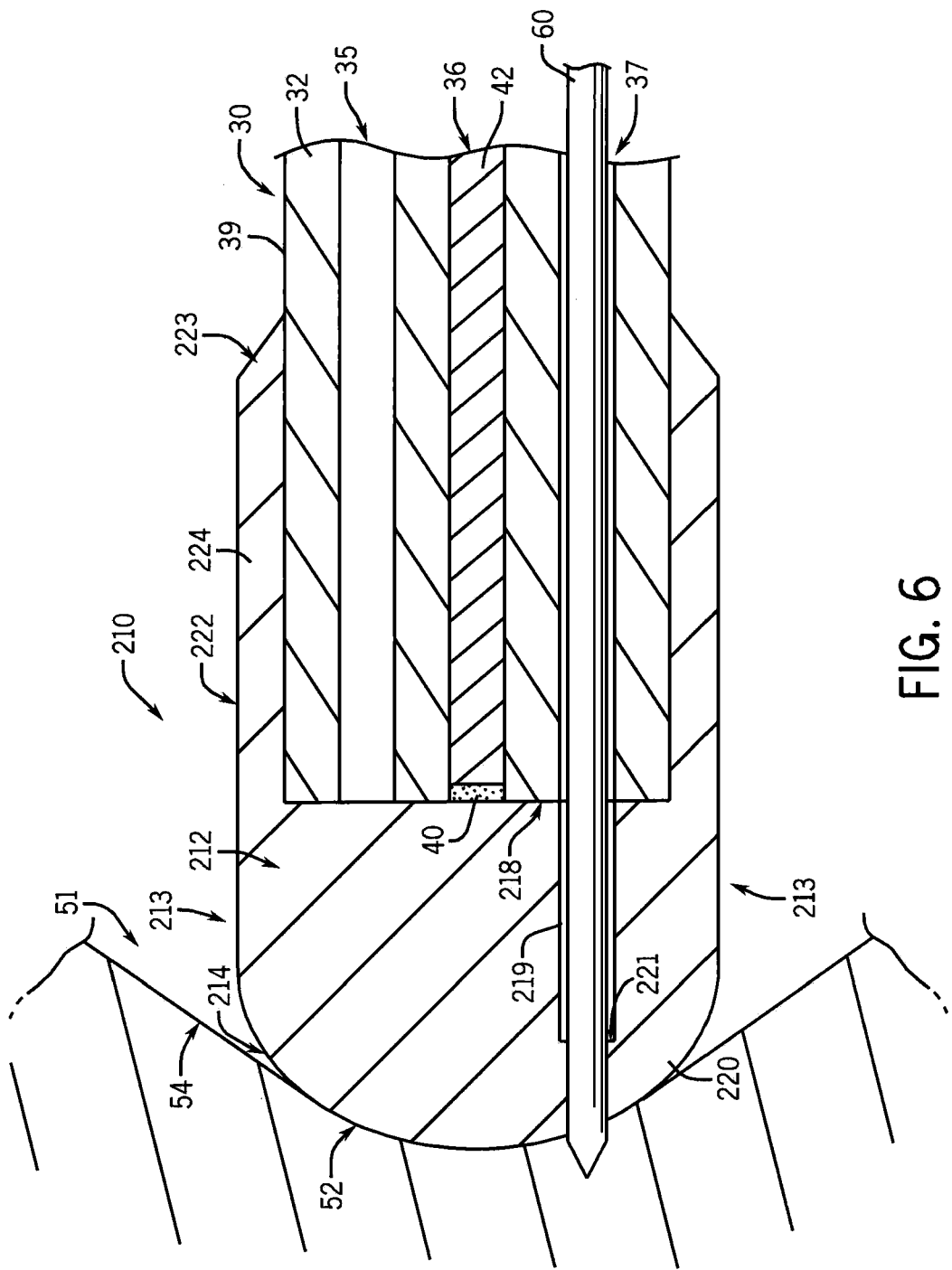
FIG. 6 is a cross-sectional view similar to FIG. 4 of the second embodiment of the optical coupler according to the invention engaging an inner wall of a body cavity wherein a medical instrument has been advanced through an instrument lumen of the endoscope, an instrument channel of the optical coupler, a solid body of the optical coupler, and against the inner wall of the body cavity.

Turning now to FIGS. 4-6, there is shown a second example embodiment of an optical coupler 210 according to the invention. The optical coupler 210 can be formed from any of the same materials as the optical coupler 10. The optical coupler 210 includes a visualization section 212 at a distal end 213 of the optical coupler 210. The visualization section 212 has an outer surface 214 with a greater degree of curvature than the embodiment shown in FIGS. 1-3. The convex, generally dome shaped outer surface 214 extends from a first outer side boundary 215 to a second opposite outer side boundary 216 of the optical coupler 210. The optical coupler 210 has a proximal surface 218, and a hollow instrument channel 219 extends from the proximal surface 218 toward the outer surface 214. A barrier section 220 of material is provided between a distal end 221 of the hollow instrument channel 219 and the outer surface 214 of the optical coupler 210. Preferably, all of the visualization section 212 (other than the hollow instrument channel 219) is a non-porous solid viscoelastic material. The instrument channel 219 is filled with an elastic material 227 different than the elastic material which comprises the visualization section 212.

The optical coupler 210 also includes an attachment section 222 connected to and extending away from the visualization section 212. The attachment section 222 is at the proximal end 223 of the optical coupler 210. In the embodiment shown, the attachment section 222 is in the form of a cylindrical wall 224. The proximal surface 218 and the cylindrical wall 224 of the optical coupler 210 define a hollow cylindrical opening 225 of the optical coupler 210.

The optical coupler 210 can be mounted on an endoscope 30. The endoscope 30 has a distal end 31 that is inserted in the hollow cylindrical opening 225 of the optical coupler 210. The endoscope 30 has a sheath 32 with an outer surface 33 that snugly engages the cylindrical wall 224 of the optical coupler 210. An end surface 34 of the endoscope 30 sealingly engages the proximal surface 218 of the optical coupler 210. The endoscope 30 includes a first lumen 35 and a second lumen 36 and a third lumen 37 that extend from the end surface 34 of the endoscope 30 to a proximal end (not shown) of the endoscope. A light guide 39 is positioned in the first lumen 35 for transmitting light toward a surface area at or beyond the outer surface 214 of the optical coupler 210. An object lens 40 is positioned at a distal end of an image carrying fiber 42, and the lens 40 is optically connected to the image carrying fiber 42 for receiving light that has been reflected from the surface area. The object lens 40 and the image carrying fiber 42 are located in the second lumen 36. The third lumen 37 aligns with the hollow instrument channel 219 of the optical coupler 210 when the optical coupler 210 is mounted on the endoscope 30. In the embodiment shown, the instrument channel 219 and the third lumen 37 have the same size inner diameter within a tolerance of ±5%.

The endoscope 30 can have a field of view of A degrees (e.g., 90-170°) as shown in FIG. 4. In FIG. 4, a portion of the outer surface 214 of the visualization section 212 is dome-shaped, and the portion of the outer surface 214 of the visualization section 212 that is dome-shaped is within the field of view of the endoscope 30. This provides for improved imaging with an increased working space as organs can be pushed out of the field of view.

Still referring to FIGS. 5 and 6, after the physician mounts the optical coupler 210 on the endoscope 30, the endoscope is inserted into a body cavity 51. The optical coupler 210 is placed in contact with a region 52 of the wall 54 of the body cavity 51 thereby displacing opaque fluid and/or particulate matter in contact with or adjacent the region. Light is transmitted from a light source through the light guide 39 in a conventional manner. The light then passes through the optical coupler 210 and onto the region 52. Reflected light then passes back through the optical coupler 210 and the lens 40 receives the reflected light from the region 52. The lens 40 transmits an optical image to the image carrying fiber 42 which transmits the optical image to an eyepiece or video display in a conventional manner.

The physician then inserts a medical instrument 60 in direction B (see FIG. 5) in the third lumen 37 of the sheath 32 of the endoscope 30. The medical instrument 60 is passed through the instrument channel 219 in the coupler 210 and then the medical instrument 60 is pierced through the barrier section 220 and the outer surface 214 of the coupler 210. A medical procedure can then be performed using the medical instrument 60 on the region 52 of the wall 54 of the body cavity 51. Non-limiting examples of the medical instrument 60 include a biopsy forceps, an electrocauterization device, an ablation device, and a suturing or stapling device. Optionally, viewing optics can be pierced through the barrier section 220 and the outer surface 214 of the coupler 210.

Figure 7:
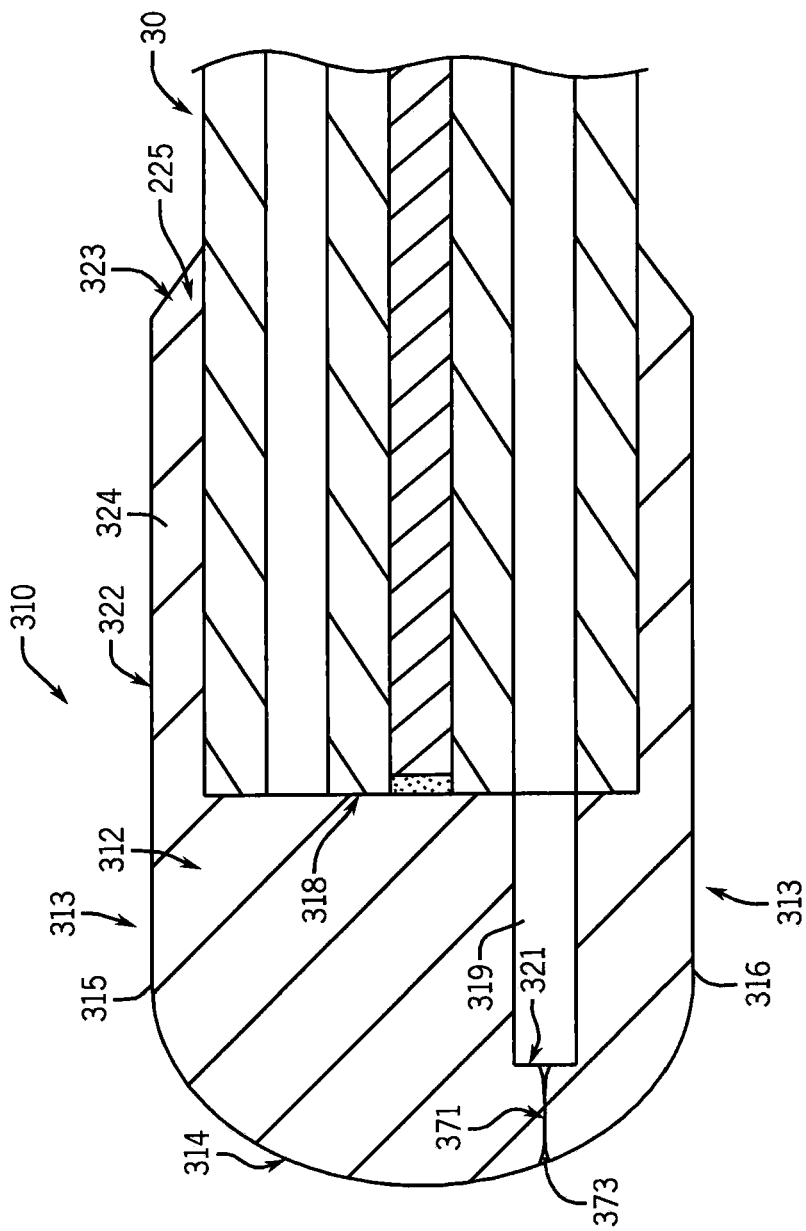
FIG. 7 is a cross-sectional view similar to FIG. 3 of a third embodiment of an optical coupler according to the invention, the optical coupler being attached to an endoscope.

Turning now to FIG. 7, there is shown a third example embodiment of an optical coupler 310 according to the invention. The optical coupler 310 can be formed from any of the same materials as the optical coupler 10. The optical coupler 310 can be mounted on an endoscope 30. The optical coupler 310 includes a visualization section 312 at a distal end 313 of the optical coupler 310. The visualization section 312 has a generally dome shaped outer surface 314 that extends from a first outer side boundary 315 to a second opposite outer side boundary 316 of the optical coupler 310. The optical coupler 310 has a proximal surface 318, and a hollow instrument channel 319 extends from the proximal surface 318 toward the outer surface 314. The optical coupler 310 also includes an attachment section 322 connected to and extending away from the visualization section 312. The attachment section 322 is at the proximal end 323 of the optical coupler 310. In the embodiment shown, the attachment section 322 is in the form of a cylindrical wall 324. The proximal surface 318 and the cylindrical wall 324 of the optical coupler 310 define a hollow cylindrical opening 325 of the optical coupler 310.

In the optical coupler 310, a narrowed passage 373 is provided at the distal end 321 of the hollow instrument channel 319. A self-sealing membrane 371 seals the narrowed passage 373 of the hollow instrument channel 319. The membrane 371 can be pierced by the medical instrument 60 and the membrane 371 reseals after withdrawal of the instrument 60 from the membrane 371.

Turning now to FIGS. 10 and 11, an optical coupler 10 similar to the coupler displayed in FIGS. 1-3 is shown, however, the coupler 10 does not have an instrument channel 19 and has an electrocauterization device 75. The electrocauterization device 75 in the optical coupler 10 includes a wire 27 extending through the visualization section 12 which connects with an electrode 26 on the outer surface 14. The wire 27 and electrode 26 may be molded into the materials forming the optical coupler 10 during the manufacturing process of the coupler 10. Other instruments may also be molded into the optical coupler 10 in this fashion as well. Doing so would provide an optical coupler 10 that is simple and inexpensive to manufacture, as well as a coupler 10 with a lesser chance that air, fluid, and/or foreign matter from the surrounding environment will enter the coupler 10 when it is attached to an endoscope, camera, or other device. Instead of molding the wire 27 and electrode 26 into the coupler 10, the wire 27 and electrode 26 may be delivered through the visualization section 12 of the coupler 10 after the coupler 10 is formed, due to the properties and characteristics of the coupler 10. Of course, instruments other than or in addition to the electrocauterization device 75 may be delivered through the coupler 10 when the coupler 10 does not have an instrument channel 19.

However, the wire 27 attached to the electrode 26 may also be configured in an optical coupler 10 that also includes one or more instrument channels 19. The wire 27 may be embedded in the visualization section 12 and run parallel and close to the hollow instrument channel 19. Alternatively, the wire 27 may pass through the visualization section 12 in an instrument channel 19.

In one non-limiting example coupler for use in endoscopic gastrointestinal procedures, the durometer of the coupler is about 15 on a Shore OO scale, if the tissue is delicate. Necrotic friable tissue requires a softer durometer and therefore, a durometer less than 6 may be desired. The coupler requires enough compression and flexural strength to displace fluids. If examining a stomach with multi folds, a durometer of 50 on a Shore OO scale may be desirable. The coupler should have optical clarity in the visible light range 400-750 nanometers. For Photodynamic Therapy, IR or florescence studies different ranges of light transmission, absorption or refraction may be beneficial.

Other non-limiting example specifications for a coupler used as an adjunct for gastrointestinal procedures are as follows: Biocompatible, single use; or made for multiple uses. Flexibility: durometer range from 2-80, Shore OO scale; Minimal optical absorption (<0.1%); Index of refraction: approximately 1.40-1.50, but may be matched to the endoscope light transmission, water, air, or whatever Index of refraction bests reduces lens surface reflections; Tensile strength: minimum, strong enough to displace fluid and tough enough to resist tearing; Elastic and self-sealing; Hydrophobic: surface repellant; Hydrophilic: within the matrix structure; High thermal resistance: will not melt with heat (500° F.-1200° F.) from electrocautery or radio ablation; and Autoclavable: at 250° F.-273° F.

Figure 12A:
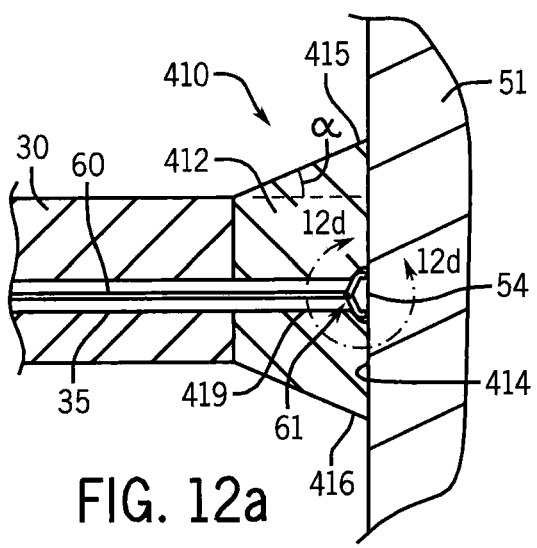
FIG. 12a is a cross-sectional view of another embodiment of an optical coupler attached to an endoscope with a biopsy forceps placed through the endoscope and into the optical coupler, the jaws of the biopsy forceps being opened.
Figure 12D:
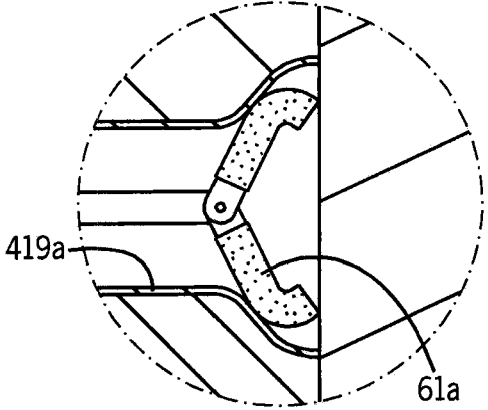
Figure 12B:
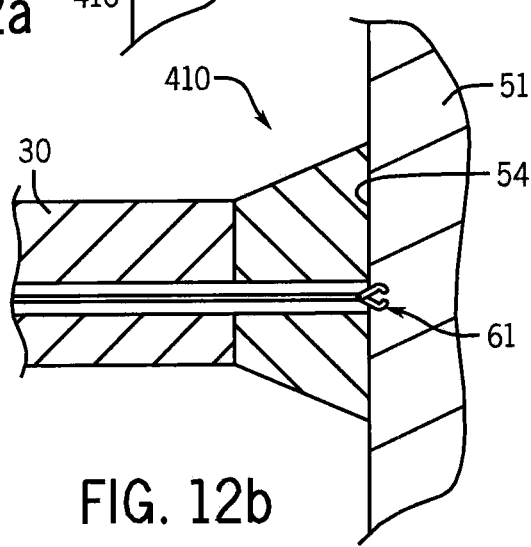
FIG. 12b is a cross-sectional view of the embodiment in FIG. 12a, with the jaws of the biopsy forceps closed to take a biopsy sample.
Figure 12C:
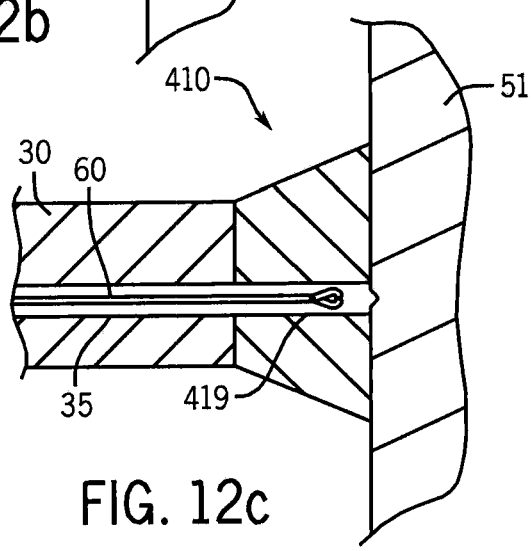
FIG. 12c is a cross-sectional view of the embodiment in FIGS. 12a and 12b, with the biopsy forceps being withdrawn after having taken the biopsy sample.

Turning now to FIGS. 12a-12c, another embodiment of an optical coupler 410 is shown mounted on an endoscope 30. The optical coupler 410 can be formed from any of the same materials as the optical couplers previously described 10, 210, 310. The optical coupler 410 includes a visualization section 412 with a first outer boundary 415 and a second outer boundary 416 and a hollow instrument channel 419 that extends through the visualization section 412 to an outer surface 414. As shown in FIGS. 12a-12c, the first and second outer boundaries 415, 416 extend at an angle α from the outer surface of the endoscope 30.

A biopsy forceps 60 is inserted into a first lumen 35 in the endoscope 30 and is passed through the instrument channel 419 in the optical coupler 410. The endoscope 30 may be configured to have other lumens as described in previous embodiments. In FIG. 12a, the jaws 61 of the biopsy forceps 60 are opened near the outer surface 414 of the visualization section 412. Because the visualization section 412 is composed of elastic materials, the visualization section 412 may expand when the jaws 61 are opened to take a biopsy sample of tissue from a wall 54 of the body cavity 51, as illustrated in FIG. 12a. The forceps 60 cannot be opened in the fixed diameter of the lumen 35 of the endoscope 30. When the jaws 61 of the forceps 60 are opened, the hinged jaws 61 can trap material comprising the coupler 410, possibly hindering functionality of the forceps 60. To alleviate this hindrance, the instrument channel 419 may be lined with a clear, flexible tube 419a and/or the jaws 61 of the forceps 60 may be covered with a soft, flexible sleeve 61a, as illustrated in FIG. 12d.

The biopsy sample is captured and removed from the wall 54 of the body cavity 51 as shown in FIGS. 12b and 12c. FIG. 12b shows the jaws 61 of the biopsy forceps 60 closing and taking a biopsy sample of tissue from a wall 54 of the body cavity 51. Then, as shown in FIG. 12c, the biopsy forceps 60 with the biopsy sample may be removed from the endoscope 30 by passing through the instrument channel 419 and the lumen 35. After the biopsy sample is withdrawn and inspected, the instrument channel 419 can be used to place a coagulation device at the exact biopsy site on the wall 54 or to reinsert the biopsy forceps 60 to obtain an additional biopsy sample.

Other types of biopsy forceps and graspers that can be used with the couplers described herein include, but are not limited to: oval cups, long oval cups, long oval cups with spike, serrated cups, serrated cups with spike, alligator graspers, elongated rat tooth "stent remove", rat tooth graspers, three nail graspers, tripod graspers, fork 1×2 graspers. Of course, other medical tools 60 other than biopsy forceps and graspers can be used with the couplers described herein.

As previously mentioned, the optical coupler could be used in non-medical applications. FIGS. 13-15 show two such examples of environments and applications of where the optical coupler may be employed.

Figure 13A:
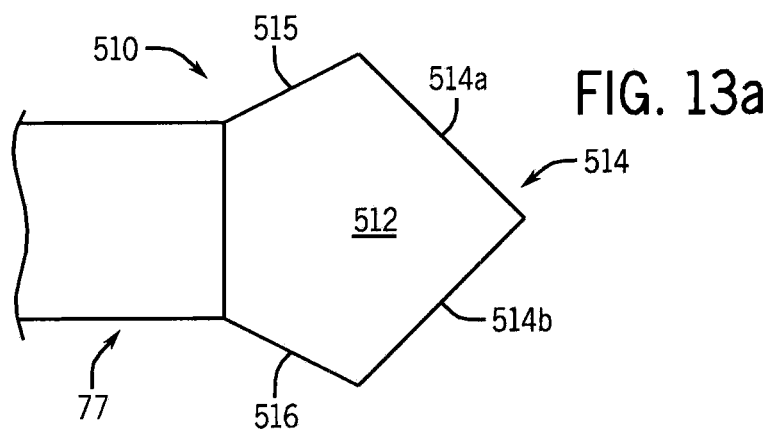
FIG. 13a is a side view of another embodiment of an optical coupler where the outer surface of the optical coupler is angled.
Figure 13B:
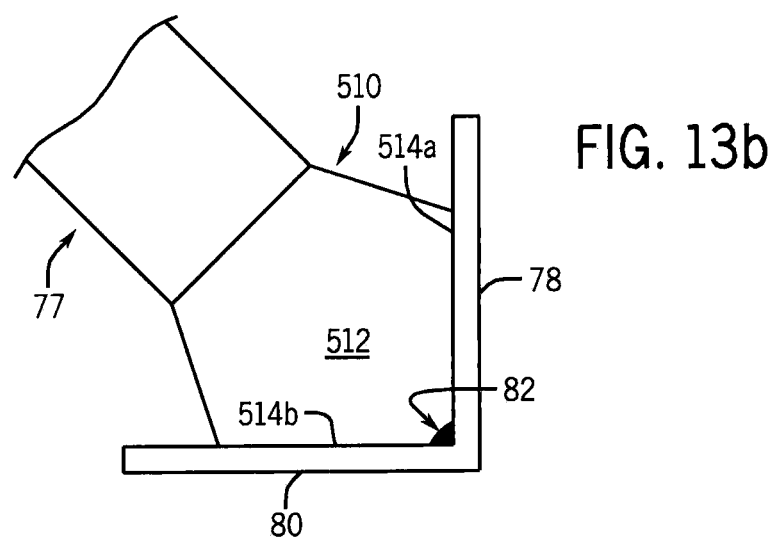
FIG. 13b is a side view of the embodiment in FIG. 13a, where the optical coupler is inspecting a weld.

Turning first to FIGS. 13a and 13b, an optical coupler 510 is shown mounted to a borescope 77. The optical coupler 510 may be used for inspecting surfaces or objects covered by opaque liquids or particulate materials. The optical coupler 510 can be formed from any of the same materials as referenced for the optical couplers previously described 10, 210, 310, 410. The optical coupler 510 has a visualization section 512 that has a first outer boundary 515, a second outer boundary 516, and an outer surface 514 that extends continuously from the first outer boundary 515 to the second outer boundary 516. The first and second outer boundaries 515, 516 extend outwards from the borescope 77 at an angle, similar to the boundaries 415, 416 shown in FIGS. 12a-12c above. The outer surface 514 is angled, such that it is composed of a first segment 514a and a second segment 514b. If desired, the optical coupler 510 may be configured with other features as previously described, such as an instrument channel.

As shown in FIG. 13b, the optical coupler 510 is designed such that the first and second segments 514a, 514b of the outer surface 514 will displace opaque liquid or particulate materials in a corner of two plates 78, 80 that may render viewing the plates 78, 80 difficult. This coupler 510 design may be beneficial for viewing a weld 82 between plates 78, 80, or for viewing the surfaces of the plates 78, 80 for defects. Of course, the optical coupler 510 may be configured with other features, as previously described.

Figure 14A:
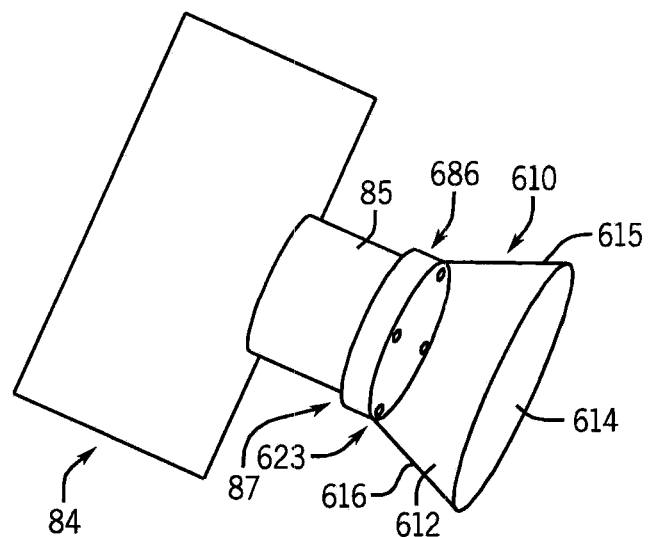
FIG. 14a is a perspective view of an optical coupler similar to the optical coupler shown in FIG. 12a-FIG. 12c, but the optical coupler is attached to a camera.
Figure 14B:
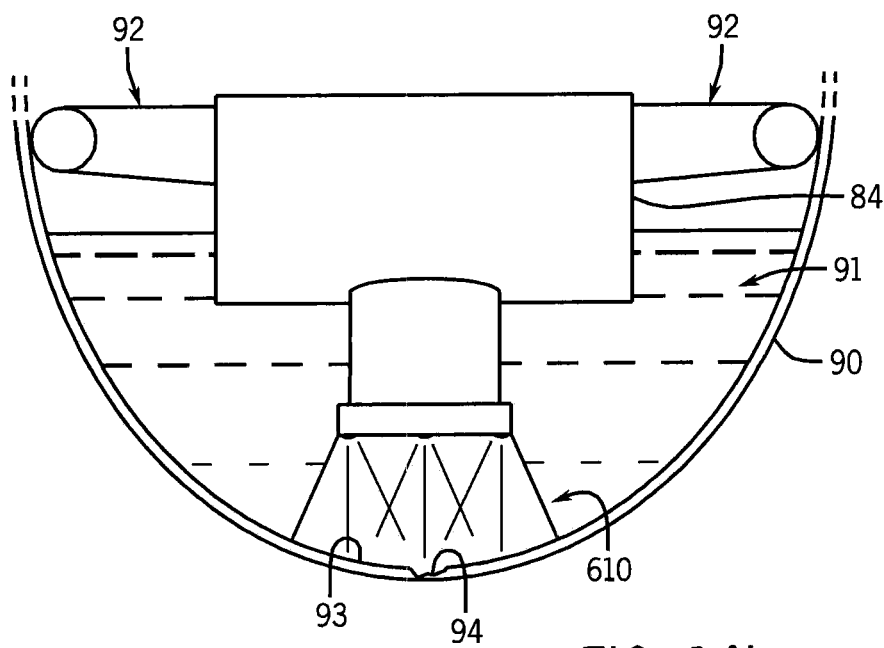
FIG. 14b is a front view of the optical coupler and camera in FIG. 14a, with the optical coupler and camera placed in a pipe filled with a liquid.
Figure 15A:
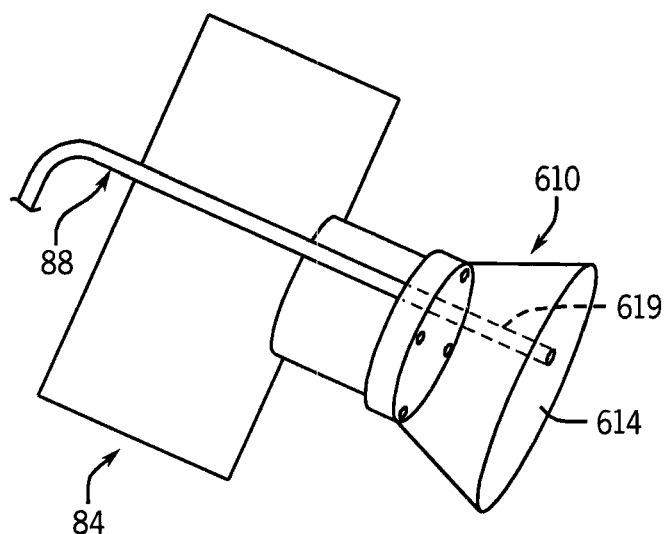
FIG. 15a is perspective view of an optical coupler and camera similar to the embodiment shown in FIGS. 14a and 14b, with a semi-rigid tube placed parallel to the camera and through the optical coupler.

FIGS. 14a, 14b, 15a, and 15b depict an optical coupler 610 mounted on a camera 84. As shown in FIG. 14a, the camera 84 has a lens 85 and may take still images, videos, or both. The optical coupler 610 can be formed from any of the same materials as referenced for the optical couplers previously described 10, 210, 310, 410, 510. The optical coupler 610 has a visualization section 612, a first outer boundary 615, a second outer boundary 616, and an outer surface 614 that extends continuously from the first outer boundary 615 to the second outer boundary 616. A light ring 686 is attached to an outer surface 87 of the lens 85 of the camera 84, near the proximal end 623 of the coupler 610. As shown in FIG. 15a, the optical coupler 610 may also include an instrument channel 619 such that a semi rigid tube 88 may be placed parallel to or through the camera 84 and through the instrument channel 619. Alternatively, the coupler 610 may not have an instrument channel 619 and the tube 88 may be pierced through the visualization section 612. The tube 88 may extend to the outer surface 614 of the optical coupler 610.

Figure 15B:
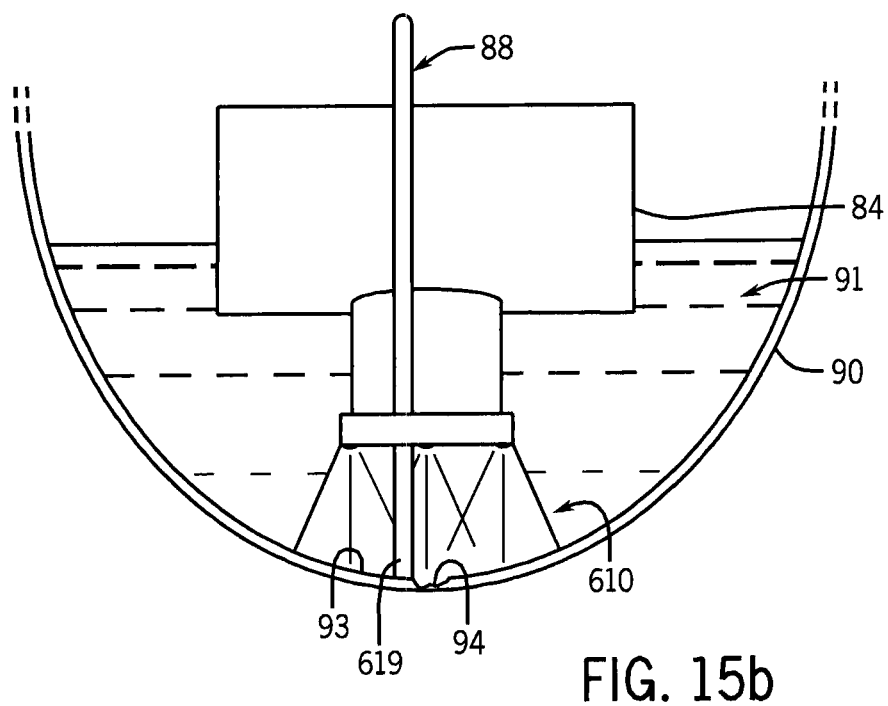
FIG. 15b is a front plan view of the optical coupler and camera in FIG. 15a, with the optical coupler and camera examining a defect in a pipe filled with liquid.

As shown in FIGS. 14b and 15b, the camera 84 and optical coupler 610 may be placed in a pipe 90 that is filled with an opaque liquid 91, such as oil. The camera 84 may be moved through the use of motorized platform 92 to view the internal surface 93 of the pipe 90 to search for defects 94. As shown in FIG. 15b, the semi rigid tube 88, fixed parallel to the camera 84 and placed through the coupler 610, may be used to deliver adhesives, cements, or the like to the defect area 94 to repair the defect.

Figure 16:
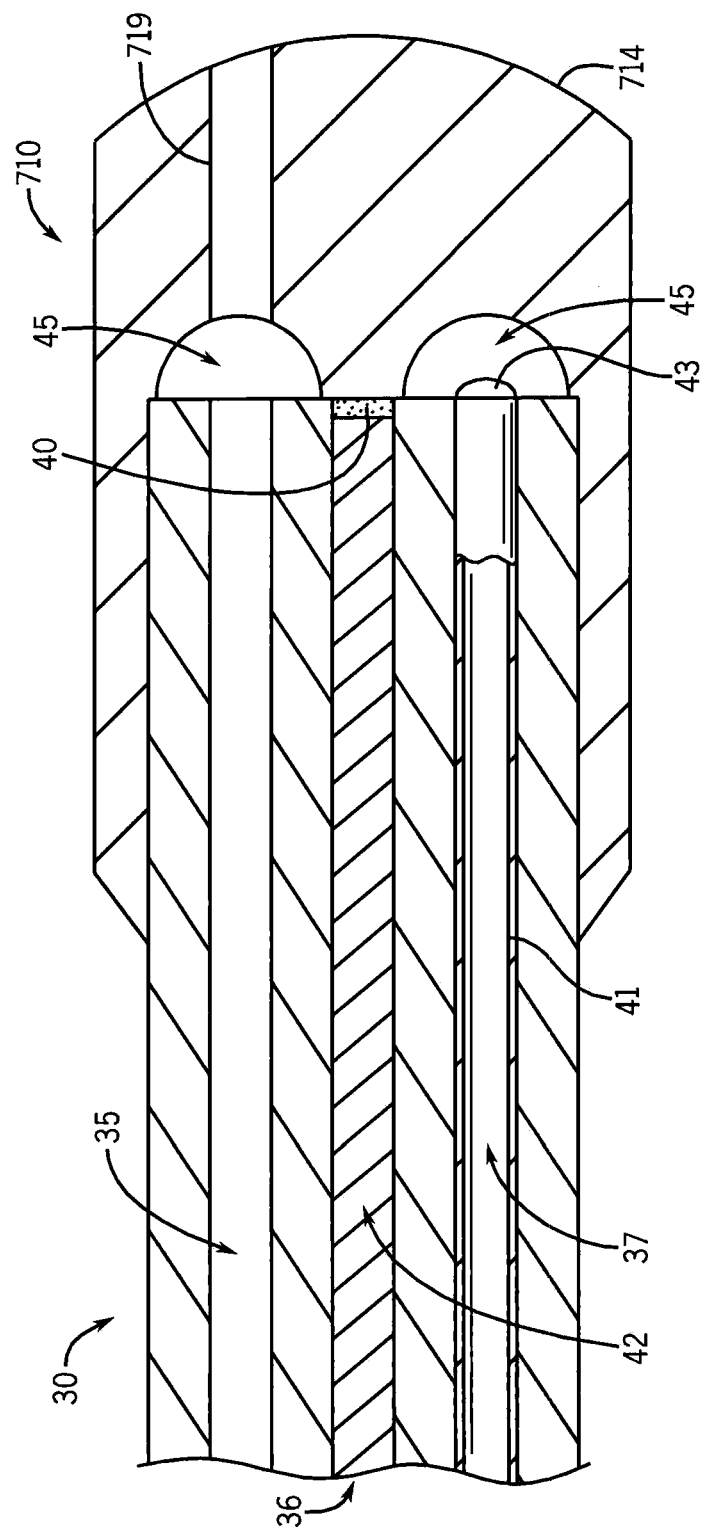
FIG. 16 is a cross-sectional view of another embodiment of an optical coupler attached to an endoscope that has an auxiliary fluid channel.

Another optical coupler 710 is shown in FIG. 16. The optical coupler 710 is mounted on an endoscope 30. A first lumen 35 of the endoscope 30 aligns with an instrument channel 719 in the coupler 710. A second lumen 36 provides access for an image carrying fiber 42 connected to a lens 40, which contacts the coupler 710. A third lumen 37 provides an auxiliary fluid channel 41 in the endoscope 30. A nozzle 43 is provided at the distal end of the auxiliary fluid channel 41. The optical coupler 710 includes an annular chamber 45 that can receive fluid 47 from the auxiliary fluid channel 41 and nozzle 43, and allow the fluid to pass through the instrument channel 719 in the coupler 710. Fluid 47 can be a clear fluid, such as a water or saline to rinse away debris in the field of view or to clean the outer surface 714 of the coupler 730.

FIGS. 17a-17c illustrate a coupler 810 having a concave outer surface 814 and a first lumen 835 that is mounted to an endoscope 30. As shown in FIGS. 17a-17c, as the coupler 30 is moved toward the wall 54 of a body cavity 51, an opaque liquid 91 (such as trapped blood) can become trapped between the outer surface 814 and the wall 54 and restrict the field of view of the endoscope 30. The coupler 810 includes an instrument channel 819 that is aligned with the first lumen 835. Thus, fluid 47 can be flushed through the endoscope 30 via the first lumen 835 and through the instrument channel 819 in coupler 810. Although not shown, fluid 47 can alternatively and/or additionally be flushed through the endoscope 30 via an auxiliary fluid channel in the endoscope 30, similar to that as described above with respect to FIG. 16. When the pressure of the introduced fluid 47 exceeds the pressure exerted by the coupler 810 against the wall 54 of the body cavity 51, the fluid 47 will flush the trapped opaque liquid 91 from the area between the outer surface 814 and the wall 54 to allow for unrestricted view of the wall 54. Additionally, because the coupler 810 can be comprised of soft materials, the coupler 810 can allow the endoscope 30 to view and perform activities on the wall 54 of the body cavity 51 with an unrestricted field of view with the application of less force being applied to the wall 54. With a gel lens attached to the endoscope, injection of a therapeutic can be accomplished after tissue contact. After the lesion has been cut free by an endoscopic tool such as an electro cautery knife or wire snare, the detached lesion can be removed by applying suction through the instrument channel.

Figure 18A:
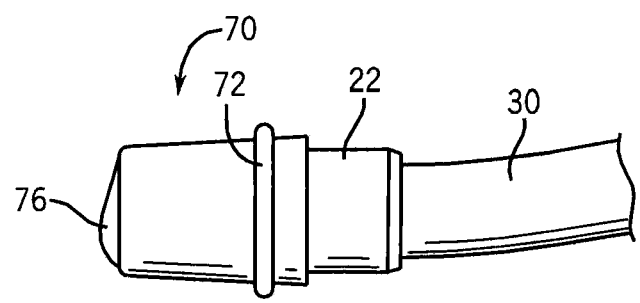
FIG. 18a is a side plan view of a coupler attached to an endoscope with the use of a cap.
Figure 18B:
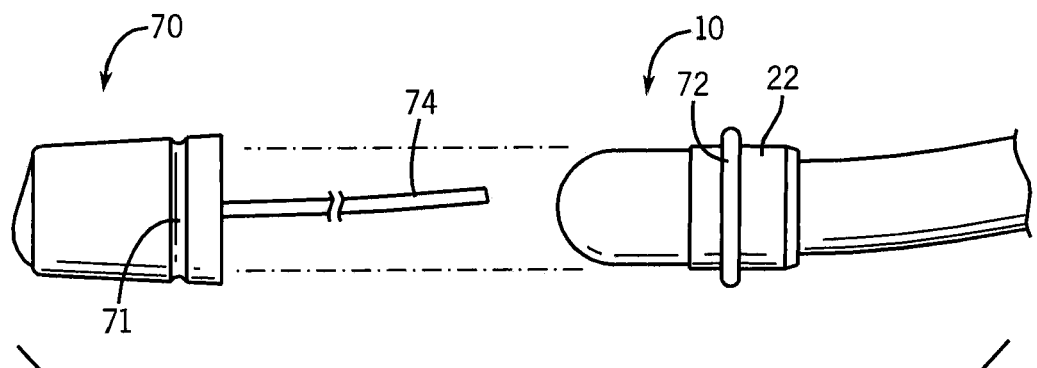

To facilitate attachment to an endoscope 30, the coupler 10 can be packaged with a cap 70 as illustrated in FIGS. 18a and 18b. The cap 70 can be secured over the coupler 10 as illustrated in FIG. 18a. The cap 70 protects the coupler 10 from dust and finger prints when handling and the cap preferably has a clear top 76. The cap 70 also includes a rod 74 that extends away from the cap 70 in a direction opposite the cover 76. The rod 74 is used to align the coupler to the endoscope 30 and can enter the instrument channel 19 of the coupler 10. Once the cap 70 is placed on the coupler 10, the o-ring 72 that resides in a circumferential groove 71 in the cap 70A can be slid down to the visualization section 22 of the coupler 10 to assist in retaining the coupler 10 on the endoscope 30. An alternative cap (not shown) for the coupler 10 could be to shrink wrap clear plastic wrap over the coupler 10 after the rod 74 has been placed through the instrument channel 19 of the coupler 10.

Coupler according to the present invention can also be used with rigid endoscopes 30. As illustrated in FIG. 19, a coupler 10 is attached to a rigid endoscope having a 0° end surface 34 and a field of view A. Due to the optical structure of most rigid endoscopes, internal lumens for instruments or fluid channels are not possible. A channel 49 that runs parallel to the outer surface of the endoscope 30 can be attached to the endoscope, directed though the sides of the coupler 10, and exit at an angle though the outer surface 14 of the coupler 10. Due to the angled nature of the channel 49, instruments passed through the channel 49 may remain visible by the operator and closer to the center of the filed of view A of the endoscope 30. If the endoscope 30 has an angled end surface 34, as illustrated in FIG. 20, the channel 49 may be straight in order to remain closer to the center of the field of view B of the endoscope 30. A small lens imbedded in the surface of the gel lens that contacts the endoscope fibers could re-aim the light or diffuse the light to reduce surface reflections on gel lens.

Figure 21:
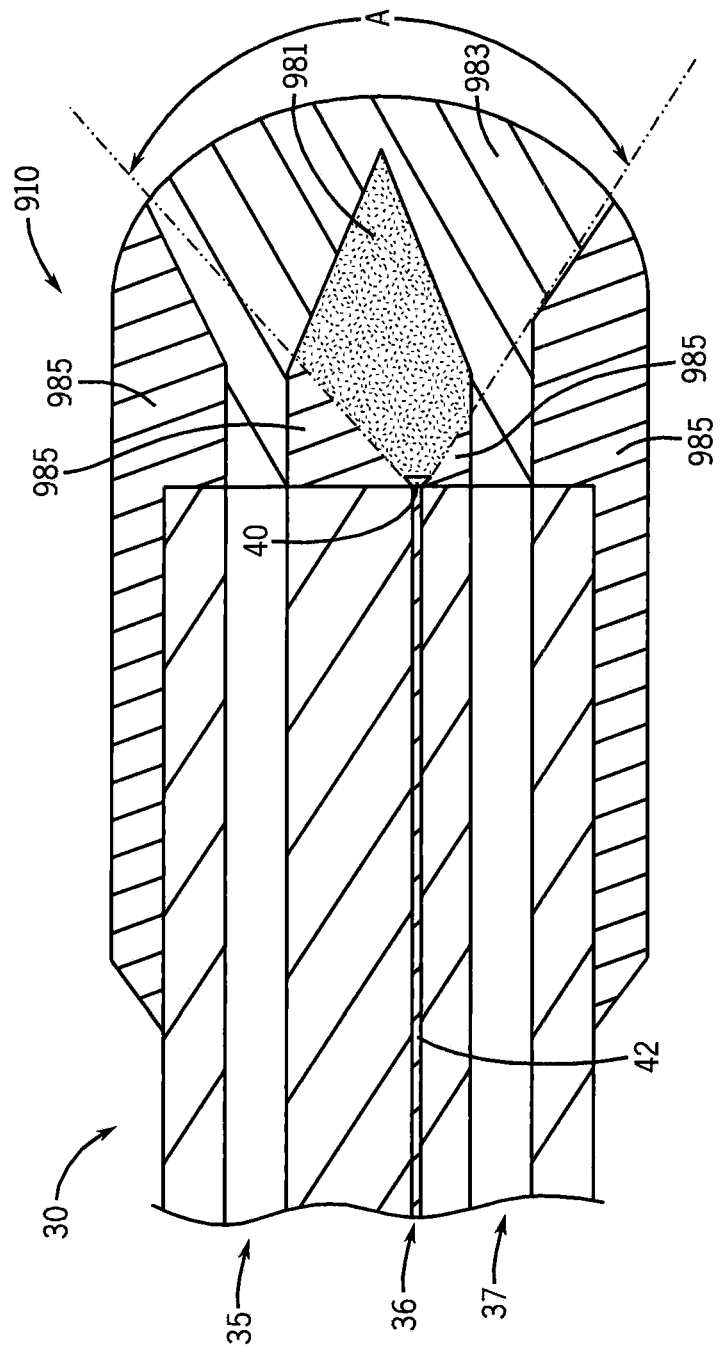
FIG. 21 is another embodiment of a coupler attached to an endoscope, the coupler being made of multiple materials.

Turning now to FIG. 21, a coupler 910 can be comprised of more than one material. The coupler 30 can include a first lumen 35, a second lumen 36 with an image carrying fiber 42 and a lens 40, and a third lumen 37. The coupler 910 can be include a clear plastic or glass lens 40 within the field of view portion 981 of the coupler 910. The field of view portion 981 of the coupler 910 is preferably 30-40 Shore on the OO Scale and can be used to reduce light loss, magnify, decrease magnification, redirect the image, or change the focal length of the endoscope 30. Small lens or mirrors (not shown) placed in the coupler 30 near the endoscope light lens 40 will re-aim the light output, reducing reflections in the field of view A or concentrate light within the field of view A. The coupler 910 also includes an instrument channel portion 983, which is preferably 6-15 Shore on the OO Scale, and a structure portion 985, which is preferably 80 or more Shore on the OO Scale.

EXAMPLES

The following Examples have been presented in order to further illustrate the invention and are not intended to limit the invention in any way.

Example 1

A coupler in a shape similar to that of FIG. 4 was formed from Sylgard® 184 silicone elastomer available from Dow Corning Midland, Mich. USA. This silicone has an index of refraction of 1.43, and a durometer of about 80 on the Shore OO scale. A monopolar electro cauterization wire was pre molded into the coupler and wire pulled through the endoscope working channel of a Pentax EG3430 11.4 mm gastroscope. The wire was connected to a Bovie electro cauterization unit. The coupler was slipped over the distal end of the gastroscope. In the open chest of a sheep, the colonoscope was advanced in blood approaching an area to be electro coagulated and video images showed a yellow flame/spark from electrocautery with no smoke visible.

Example 2

A coupler in a shape similar to that of FIG. 4 was formed from Sylgard® 184 silicone elastomer. The coupler was attached to the end of a Pentax EG3430 11.4 mm gastroscope. Suitable video images were obtained in an electrocauterization procedure on a sheep esophagus wall.

Example 3

A coupler in a shape similar to that of FIG. 4 was formed from Sylgard® 184 silicone elastomer. The coupler was attached to the end of a Pentax EG3430 11.4 mm gastroscope. Suitable video images were obtained in a sheep stomach.

Example 4

A coupler in a shape similar to that of FIG. 4 was formed from Sylgard® 184 silicone elastomer. The coupler was attached to the end of a Pentax 2931 9.8 mm gastroscope. Suitable video images were obtained inside a sheep inferior vena cava. The portal vein entrance into the vena cava was identified. A small thrombus was also identified.

Example 5

A coupler in a shape similar to that of FIG. 1 was formed from Curing Gel OC-451A-LPH 15, a silicone-based optical curing gel available from Nye Lubricants, Inc., Fairhaven, Mass., USA. The silicone gel has an index of refraction of 1.51, and a durometer of 15 on the Shore OO scale. The coupler was attached to the end of a Pentax 9.8 mm gastroscope. Suitable video images were obtained for a swine stomach wall.

Example 6

A coupler in the shape similar to FIG. 1 was formed from a polyvinyl alcohol (PVA) solution in a mixed solvent consisting of water and dimethyl sulfoxide (DMSO). Suitable images were obtained inside the swine stomach.

Other working prototypes of couplers were made with: OCK-451-80, OCK-451-LPH, and OCK-451-LPH-15 silicone-based optical curing gels available from Nye Lubricants, Inc.; curable dimethylvinyl-terminated dimethyl siloxane available as Dow Corning CY 52-276; hydro gel lens; transparent poly (vinyl alcohol) hydrogel; a two component, low viscosity silicone compound available as Master Sil 151MED; and mineral oil and a powdered plastic.

Handheld Device

Figure 22A:
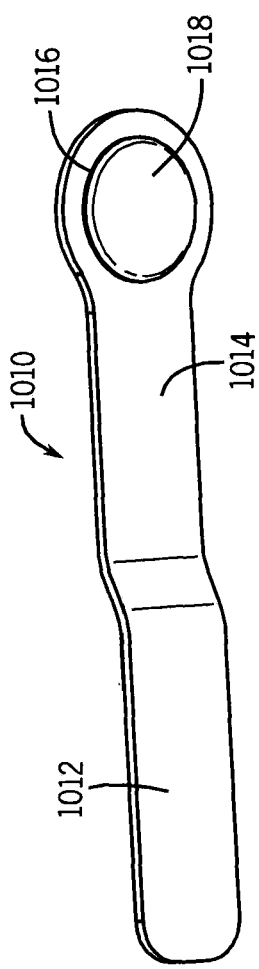
FIG. 22a is a perspective view of a coupler used in a handheld device.
Figure 22B:
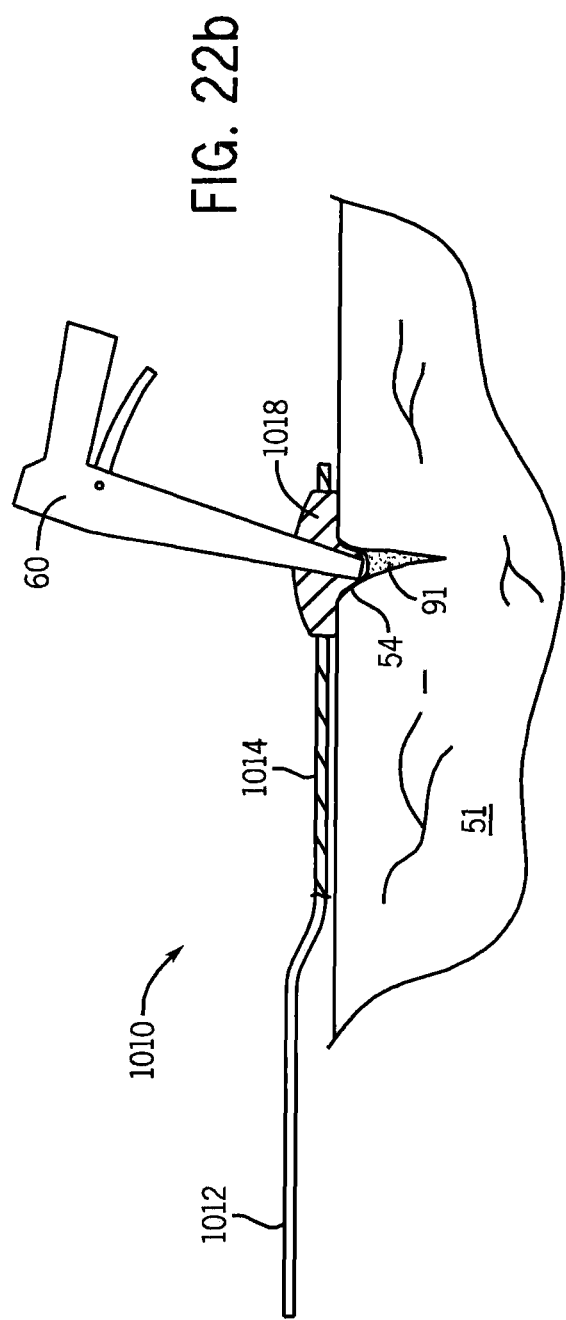
FIG. 22b is a cross-sectional view of the coupler of FIG. 22a, with a stapler passing through the coupler to treat a laceration.

Turning now to FIGS. 22*a* and 22*b*, a handheld device 1010 is shown. The handheld device 1010 includes a handle 1012, a frame 1014, and a cavity 1016 within the frame 1014. Within the cavity 1016 is a transparent section 1018 that is puncturable, or easily pierced, with surgical instruments. The transparent section 1018 can be comprised of similar materials as described above with respect to the optical couplers, and provides many of the same benefits and advantages as described above.

The handheld device 1010 may be used in a variety of circumstances. For example, the handheld device 1010 may be used to push aside an opaque liquid 91, such as blood, from the wall 54 of a body cavity 51, such as near a laceration in the skin of a patient. In doing so, the transparent section 1018 allows the physician to view the wall 54 of the body cavity 51. The pressure of the transparent section 1018 may also help coagulation. The upper and lower surfaces 1020, 1022 of the transparent section 1018 may be slightly convex as shown, flat, or concave as described above with respect to the couplers, or provided in any other desired shape. Because the transparent section 1018 can be pierced, a medical tool 60 (such as a stapler) may pass through the transparent section 1018, allowing the physician to treat the wall 54 of the body cavity 51 while the opaque liquid 91 is removed from the area of treatment. As illustrated in FIG. 22*b*, the handle 1012 may have an angle with respect to the frame 1014 to provide more room for a physician's hand when the handheld device is held near an area of treatment.

The transparent section can also be self-sealing such that the medical tool 60 can be removed without opaque liquids 91 filling the punctured section of the transparent section 1018 previously occupied by the tool 60. Additionally, the transparent section 1018 can be detachable from the handheld device 1010 such that after one use a new transparent section 1018 can be installed after sanitizing the handheld device 1010.

The transparent section can comprise a material selected from the group consisting of silicone elastomers, silicone gels, albumin based gels, mineral oil based gels, epoxies, polyurethanes, polyisoprene, polybutadiene, and mixtures thereof. The material can be a crosslinked polysiloxane. The material can be a hydrogel selected from the group consisting of polyvinyl alcohol, poly(hydroxyethyl methacrylate), polyethylene glycol, and poly(methacrylic acid).

Of course, the handheld device 1010 is not restricted to medical applications and may be used for other purposes, such as industrial applications discussed above with respect to the optical couplers.

Thus, the invention provides an optical coupler for mounting on an endoscope, borescope, camera, or the like. The coupler provides improved optical imaging of surfaces covered with opaque fluids, semisolid materials or particulate matter.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. An optical coupler for mounting at a distal end of an optical imaging device for visualizing a surface area, the coupler comprising:
   a visualization section at one end of the coupler, the visualization section including a proximal surface for engaging a distal end of the optical imaging device, the visualization section including an outer surface spaced apart from the proximal surface, the outer surface extending continuously from a first outer side boundary across to a second opposite outer side boundary of the visualization section, the visualization section comprising one or more elastic materials capable of transmitting an optical image of a surface area to be visualized and capable of allowing an instrument to be delivered through the visualization section; and
   an attachment section connected to and extending away from the visualization section, the attachment section being dimensioned to be mounted at the distal end of the optical imaging device,
   at least a surface portion of the proximal surface of the visualization section being directly in front of a light receiving element of the optical imaging device and the surface area to be visualized when the coupler is mounted to the optical imaging device,
   wherein a portion of the visualization section is non-inflatable, and
   wherein the outer surface defines a distal wall of the visualization section.

2. The optical coupler of claim 1 wherein:
   the visualization section includes an instrument channel extending from the proximal surface toward the outer surface.

3. The optical coupler of claim 2 wherein:
   the instrument channel is hollow.

4. The optical coupler of claim 2 wherein
   the instrument channel is filled with an elastic material different than the elastic material which comprises the visualization section.

5. The optical coupler of claim 2 wherein:
   the instrument channel extends from the proximal surface through the outer surface, and
   the visualization section includes a self-sealing characteristic, the characteristic enables the visualization section to be pierced by an instrument and the visualization section being re sealable after withdrawal of the instrument from the visualization section.

6. The optical coupler of claim 1 wherein:
the outer surface is spaced apart from the proximal surface by a length equal to a reference distance selected from values in a depth of field distance range of the optical imaging device.

7. The optical coupler of claim 6 wherein:
the reference distance is in the lower 10% of values in the depth of field distance range of the optical imaging device.

8. The optical coupler of claim 1 wherein:
a portion of the outer surface of the visualization section is dome-shaped and is within a field of view of the optical imaging device when the attachment section is mounted at the distal end of the optical imaging device.

9. The optical coupler of claim 1 wherein:
the material preferably has a durometer of from 40-95 on the Shore OO scale.

10. The optical coupler of claim 1 wherein:
the material preferably has a degree of light transmittance greater than 90% based on test standard ASTM D-1003.

11. The optical coupler of claim 1 wherein:
the material has an optical absorption of less than 0.1% in the visible light range.

12. The optical coupler of claim 1 wherein:
the material has an index of refraction of about 1.3 to about 1.7.

13. The optical coupler of claim 1 wherein:
the material is selected from the group consisting of silicone elastomers, silicone gels, albumin based gels, mineral oil based gels, epoxies, polyurethanes, polyisoprene, polybutadiene, crosslinked polysiloxane, polyvinyl alcohol, poly(hydroxyethyl methacrylate), polyethylene glycol, poly(methacrylic acid), and mixtures thereof.

14. The optical coupler of claim 1 wherein:
the visualization section includes a hollow instrument channel extending from the proximal surface toward the outer surface,
the visualization section includes a barrier section extending between a distal end of the instrument channel and the outer surface of the visualization section,
the barrier section includes a self-sealing characteristic, the characteristic enabling the barrier section to be pierced by an instrument and the barrier section being resealable after withdrawal of the instrument from the barrier section, and
a portion of the outer surface of the visualization section is dome-shaped and is within a field of view of the optical imaging device when the attachment section is mounted at the distal end of the optical imaging device.

15. The optical coupler of claim 1 further comprising:
a hollow instrument channel,
wherein the first outer side boundary and the second outer side boundary of the visualization section extend at an angle away from an outer surface of the optical imaging device when the attachment section is mounted at the distal end of the optical imaging device.

16. The optical coupler of claim 1 wherein:
the outer surface of the visualization section includes a first segment and a second segment that form an included angle greater than 0 degrees.

17. The optical coupler of claim 1 wherein:
the first outer side boundary and the second outer side boundary of the visualization section extend at an angle away from an outer surface of the optical imaging device when the attachment section is mounted at the distal end of the optical imaging device.

18. The optical coupler of claim 1 further comprising:
a hollow instrument channel,
wherein the visualization section includes an annular chamber in fluid communication with instrument channel.

19. The optical coupler of claim 1 wherein:
the visualization section includes one or more instrument channels extending from the proximal surface toward the outer surface.

20. The optical coupler of claim 1 further comprising:
a cap suitable for securing over the optical coupler.

21. The optical coupler of claim 20 wherein:
the cap includes a rod for aligning the optical coupler on the optical imaging device.

22. The optical coupler of claim 1 wherein:
the visualization section includes an instrument channel, and the instrument channel is flexible.

23. The optical coupler of claim 1 wherein:
the visualization section includes an instrument channel, and the instrument channel has an end section configured such that the end section of the instrument channel is angled obliquely with respect to an end surface of the optical imaging device.

24. The optical coupler of claim 23 wherein:
the end surface of the optical imaging device is angled obliquely with respect to a longitudinal axis of the optical imaging device.

25. The device of claim 1 wherein:
the optical imaging device includes an object lens positioned at a distal end of an image carrying fiber, and
the visualization section of the coupler is positioned between the lens and the surface area when visualizing the surface area.

26. A device for visualizing a surface area covered with an opaque fluid and/or particulate matter, the device comprising:
an optical imaging device; and
an optical coupler mounted at a distal end of the optical imaging device, the coupler including a visualization section at one end of the coupler, the visualization section including a proximal surface for engaging a distal end of the optical imaging device, the visualization section including an outer surface spaced apart from the proximal surface, the outer surface extending continuously from a first outer side boundary across to a second opposite outer side boundary of the visualization section, the visualization section comprising one or more elastic materials capable of transmitting an optical image of the surface area and capable of allowing an instrument to be delivered through the visualization section, and the coupler including an attachment section connected to and extending away from the visualization section, the attachment section being dimensioned to be mounted at the distal end of the optical imaging device,
at least a surface portion of the proximal surface of the visualization section being directly in front of a light receiving element of the optical imaging device and the surface area to be visualized when the coupler is mounted to the optical imaging device,
wherein a portion of the visualization section is non-inflatable, and
wherein the outer surface defines a distal wall of the visualization section.

27. The device of claim 26 wherein:
the optical imaging device includes a light guide, an image carrying fiber, and an object lens positioned at a distal end of the image carrying fiber, the lens being connected to the image carrying fiber; and the material has an index of refraction equal an index of refraction of the light guide or an index of refraction of the image carrying fiber.

28. The device of claim 26 wherein:
the optical imaging device includes a sheath with a lumen for receiving an instrument; and
the instrument is one of a biopsy forceps, an electrocauterization device, an ablation device, a suturing device, a stapling device, a light fiber, and a light guide.

29. The device of claim 26 wherein:
the visualization section includes an instrument channel, the instrument channel is configured such that the instrument channel exits the outer surface of the optical coupler near a center of a field of view of the optical imaging device.

30. The device of claim 26 wherein:
the visualization section includes an instrument molded into the visualization section.

31. A device for visualizing a surface area covered with an opaque fluid and/or particulate matter, the device comprising:
an optical imaging device;
an instrument; and
an optical coupler capable of visualization therethrough, the coupler comprising one or more elastic materials capable of transmitting an optical image of a surface area to be visualized and capable of allowing the instrument to be delivered through the coupler, the optical coupler having a visualization section including a proximal surface for engaging a distal end of the optical imaging device,
at least a surface portion of the proximal surface of the visualization section being directly in front of a light receiving element of the optical imaging device and the surface area to be visualized when the coupler is mounted to the optical imaging device,
wherein a portion of the visualization section is non-inflatable, and
wherein an outer surface of the visualization section defines a distal wall of the visualization section.

32. The device of claim 31 wherein:
the instrument is one of a biopsy forceps, an electrocauterization device, an ablation device, a suturing device, a stapling device, a light fiber, and a light guide.

33. The device of claim 31 wherein:
the instrument is a stapling device.

34. A device for visualizing a surface area covered with an opaque fluid and/or particulate matter, the device comprising:
an endoscope including an instrument and an optical imaging device; and
an optical coupler capable of visualization therethrough, the coupler comprising one or more elastic materials capable of transmitting an optical image of a surface area to be visualized and capable of allowing the instrument to be delivered through the coupler, the coupler being dimensioned to be mounted at a distal end of the endoscope, the optical coupler having a visualization section including a proximal surface for engaging a distal end of the optical imaging device,
at least a surface portion of the proximal surface of the visualization section being directly in front of a light receiving element of the optical imaging device and the surface area to be visualized when the coupler is mounted to the optical imaging device,
wherein a portion of the visualization section is non-inflatable, and
wherein an outer surface of the visualization section defines a distal wall of the visualization section.

35. The device of claim 34 wherein:
the instrument is one of a biopsy forceps, an electrocauterization device, an ablation device, a suturing device, a stapling device, a light fiber, and a light guide.

36. The device of claim 34 wherein:
the instrument is a stapling device.

* * * * *